US011510615B2

(12) United States Patent
Chopra et al.

(10) Patent No.: US 11,510,615 B2
(45) Date of Patent: Nov. 29, 2022

(54) METHODS, APPARATUSES, AND SYSTEMS FOR INDUCTIVE HEATING OF FOREIGN METALLIC IMPLANTS

(71) Applicant: THE BOARD OF REGENTS OF THE UNIVERSITY OF TEXAS SYSTEM, Austin, TX (US)

(72) Inventors: Rajiv Chopra, Dallas, TX (US); David Greenberg, Dallas, TX (US); Yonatan Chatzinoff, Dallas, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 828 days.

(21) Appl. No.: 16/247,276

(22) Filed: Jan. 14, 2019

(65) Prior Publication Data

US 2019/0159725 A1    May 30, 2019

Related U.S. Application Data

(63) Continuation of application No. PCT/US2017/042156, filed on Jul. 14, 2017.
(Continued)

(51) Int. Cl.
*A61B 5/00* (2006.01)
*A61B 5/01* (2006.01)
(Continued)

(52) U.S. Cl.
CPC .......... *A61B 5/4851* (2013.01); *A61B 5/0071* (2013.01); *A61B 5/01* (2013.01);
(Continued)

(58) Field of Classification Search
CPC ............... A61B 5/4851; A61B 5/0071
(Continued)

(56) References Cited

U.S. PATENT DOCUMENTS

| 4,658,836 A | 4/1987 | Turner |
| 4,945,912 A | 8/1990 | Langerberg |

(Continued)

FOREIGN PATENT DOCUMENTS

| CA | 2697012 | 1/2009 |
| CN | 102247619 A | 11/2011 |

(Continued)

OTHER PUBLICATIONS

European Patent Office, Search Report dated Nov. 24, 2020 in European Patent Application No. 17828539.1 (10 pages).
(Continued)

*Primary Examiner* — Nadia A Mahmood
(74) *Attorney, Agent, or Firm* — Trop, Pruner & Hu, P.C.

(57) ABSTRACT

Methods, apparatuses, systems, and implementations for inductive heating of a foreign metallic implant are disclosed. A foreign metallic implant may be heated via AMF pulses to ensure that the surface of the foreign metallic implant heats in a uniform manner. As the surface temperature of the foreign metallic implant rises, acoustic signatures may be detected by acoustic sensors that may indicate that tissue may be heating to an undesirable level approaching a boiling point. Once these acoustic signatures are detected, the AMF pulses may be shut off for a time period to allow the surface temperature of the implant to cool before applying additional AMF pulses. In this manner, the surface temperature of a foreign metallic implant may be uniformly heated to a temperature adequate to treat bacterial biofilm buildup on the surface of the foreign metallic implant without damaging surrounding tissue. The AMF pulse treatment can be combined with an antibacterial/antimicrobial treatment regimen to reduce the time and/or antibacterial dosage amount needed to remove the biofilm from the metallic implant.

17 Claims, 22 Drawing Sheets

Related U.S. Application Data

(60) Provisional application No. 62/445,963, filed on Jan. 13, 2017, provisional application No. 62/362,402, filed on Jul. 14, 2016.

(51) Int. Cl.
*A61N 1/378* (2006.01)
*A61N 1/40* (2006.01)
*A61B 8/08* (2006.01)
*A61F 2/30* (2006.01)
*A61N 1/02* (2006.01)
*A61N 2/02* (2006.01)

(52) U.S. Cl.
CPC ............ *A61B 5/412* (2013.01); *A61B 5/4528* (2013.01); *A61B 5/4836* (2013.01); *A61B 8/0841* (2013.01); *A61F 2/30* (2013.01); *A61N 1/025* (2013.01); *A61N 1/378* (2013.01); *A61N 1/40* (2013.01); *A61N 1/403* (2013.01); *A61N 1/406* (2013.01); *A61F 2002/30668* (2013.01); *A61F 2002/30719* (2013.01); *A61F 2002/30932* (2013.01); *A61N 2/02* (2013.01)

(58) Field of Classification Search
USPC ........................................................ 607/102
See application file for complete search history.

(56) References Cited

U.S. PATENT DOCUMENTS

| | | |
|---|---|---|
| 5,427,846 A | 6/1995 | McGaffigan |
| 5,468,210 A | 11/1995 | Matsui et al. |
| 5,720,775 A | 2/1998 | Larnard |
| 5,827,269 A | 10/1998 | Saadat |
| 6,423,953 B1 | 7/2002 | Johnson, Jr. |
| 6,475,434 B1 | 11/2002 | Darouiche |
| 6,599,234 B1 | 7/2003 | Gray et al. |
| 6,786,904 B2 | 9/2004 | Doscher et al. |
| 6,808,535 B1 | 10/2004 | Jordan |
| 7,025,778 B2 | 4/2006 | Hayashi et al. |
| 7,174,217 B2 | 2/2007 | Rioux et al. |
| 7,731,648 B2 | 6/2010 | Ivkov |
| 7,744,604 B2 | 6/2010 | Maitland et al. |
| 7,918,883 B2 | 4/2011 | Weber |
| 7,951,061 B2 | 5/2011 | Foreman et al. |
| 7,967,839 B2 | 6/2011 | Flock et al. |
| 8,048,471 B2 | 11/2011 | Nesbitt |
| 8,114,345 B2 | 2/2012 | Dlugos, Jr. et al. |
| 8,182,859 B2 | 5/2012 | Atanasoska et al. |
| 8,565,892 B2 | 10/2013 | Nayfach-Battilana |
| 8,620,431 B2 | 12/2013 | Fuller et al. |
| 8,805,536 B2 | 8/2014 | Li et al. |
| 9,039,697 B2 | 5/2015 | Lischinsky et al. |
| 9,060,761 B2 | 6/2015 | Hastings et al. |
| 9,078,655 B2 | 7/2015 | Manwaring et al. |
| 9,220,557 B2 | 12/2015 | Manwaring et al. |
| 9,561,066 B2 | 2/2017 | Sharma et al. |
| 9,636,495 B2 | 5/2017 | Szasz et al. |
| 9,827,035 B2 | 11/2017 | Schwagten et al. |
| 10,149,712 B2 | 12/2018 | Manwaring et al. |
| 2002/0066702 A1 | 6/2002 | Liu |
| 2004/0167506 A1 | 8/2004 | Chen |
| 2004/0210282 A1 | 10/2004 | Flock et al. |
| 2005/0021088 A1 | 1/2005 | Schuler et al. |
| 2005/0261763 A1 | 11/2005 | Wang et al. |
| 2006/0155345 A1 | 7/2006 | Williams et al. |
| 2007/0010702 A1 | 1/2007 | Wang et al. |
| 2007/0027460 A1 | 2/2007 | Case et al. |
| 2008/0319247 A1 | 12/2008 | Forbes et al. |
| 2009/0292159 A1 | 11/2009 | Litovitz |
| 2009/0319010 A1 | 12/2009 | Hirayama et al. |
| 2010/0204802 A1* | 8/2010 | Wilson ..................... A61F 2/32 623/23.6 |
| 2012/0101363 A1 | 4/2012 | Gordon et al. |
| 2014/0024882 A1 | 1/2014 | Chornenky et al. |
| 2016/0184002 A1 | 6/2016 | Yang et al. |
| 2017/0050040 A1 | 2/2017 | Trembly |
| 2017/0216623 A1 | 8/2017 | Parsai et al. |
| 2017/0216632 A1 | 8/2017 | Lee et al. |
| 2018/0153607 A1 | 6/2018 | Van Langenhove |
| 2019/0159725 A1 | 5/2019 | Chopra et al. |
| 2020/0253737 A1 | 8/2020 | Bonutti et al. |

FOREIGN PATENT DOCUMENTS

| | | |
|---|---|---|
| CN | 105596118 A | 5/2016 |
| EP | 0205851 | 12/1986 |
| EP | 0558297 | 9/1993 |
| EP | 1489985 | 12/2004 |
| EP | 2208506 | 7/2010 |
| GB | 2557900 | 7/2018 |
| JP | 2005253813 A | 9/2005 |
| WO | 1998034564 A1 | 8/1998 |
| WO | 2002000145 A1 | 1/2002 |
| WO | WO 02/058785 | 8/2002 |
| WO | WO 03/059447 | 7/2003 |
| WO | 2016025768 A1 | 2/2016 |
| WO | WO 2018/005541 | 1/2018 |

OTHER PUBLICATIONS

International Preliminary Report on Patentability Issued in Corresponding PCT Application No. PCT/US2017/042156, dated Jan. 15, 2019.
International Search Report and Written Opinion Issued in Corresponding PCT Application No. PCT/US2017/042156, dated Sep. 25, 2017.
Chinese Patent Office, Second Office Action dated Feb. 8, 2022 in Chinese Patent Application No. 201780056289.0 (9 pages).
Chinese Patent Office, Office Action dated May 7, 2021 in Chinese Patent Application No. 201780056289.0 (20 pages).
Patent Cooperation Treaty, International Search Report and Written Opinion dated Jun. 22, 2022 in PCT Patent Application No. PCT/US2022/22892 (9 pages).

\* cited by examiner

METHODS, APPARATUSES, AND SYSTEMS FOR INDUCTIVE HEATING OF FOREIGN METALLIC IMPLANTS

CROSS-REFERENCE TO RELATED APPLICATIONS

This application is a continuation application of International Application No. PCT/US2017/042156, filed Jul. 14, 2017 which claims priority to U.S. Provisional Application No. 62/362,402, filed Jul. 14, 2016, and U.S. Provisional Application No. 62/445,963, filed Jan. 13, 2017. The entire contents of both are specifically incorporated by reference herein in their entirety without disclaimer.

BACKGROUND

1. Field of the Invention

This disclosure relates generally to methods, apparatuses, and systems for inductive heating of foreign metallic implants in order to treat biofilms.

2. Description of Related Art

Prosthetic joint replacement has become an effective and widespread medical treatment for aging and damaged joints. However, prosthetic joints may be susceptible to infection due the buildup of bacterial biofilms on the joint. It is estimated that between 1% and 5% of prosthetic joint replacement patients suffer from these types of infections. Prior methods of treating these infections include additional surgeries and regiments of prescribed oral and/or intravenous (IV) antibiotics. However, these treatments may not be completely effective and may require a high amount of resources.

SUMMARY

This disclosure presents, in part, methods and systems of preventing and treating prosthetic joint infections that are non-surgical and non-invasive, that are repeatable, and that are usable with a wide range of implanted devices. In some embodiments, a system for treating a surface of a foreign metallic implant is provided. For purposes of this disclosure, although the claimed system has a useful application of treating a foreign metallic implant, the system is not limited in this way, nor is the foreign metallic implant itself intended to be part of the claimed system. In some embodiments, the system includes one or more external transmitter devices including an alternating magnetic field (AMF) transmitter configured to apply one or more AMF pulses to the foreign metallic implant. In some embodiments, the system further includes one or more external acoustic sensor devices configured to receive one or more acoustic emission signatures from tissue located in a vicinity of the foreign metallic implant. In some embodiments, the system further includes a control system having at least one processor configured to enable the one or more external transmitter devices to apply one or more AMF pulses to the foreign metallic implant for one or more of a predetermined time period, a predetermined pulse duration, a predetermined pulse repetition frequency, and at a predetermined power level; receive one or more signals from the one or more external acoustic sensor devices; determine that the one or more signals correspond to one or more acoustic emission signatures that indicate that a temperature of the foreign metallic implant is sufficient to disrupt a biofilm matrix on a surface of the foreign metallic implant; and enable one or more antibiotic or antimicrobial treatments to be applied to the foreign metallic implant.

In some embodiments, the control system is further configured to enable the one or more external transmitter devices to shut off for a predetermined delay period after applying the one or more AMF pulses. In some embodiments, the control system is further configured to enable the one or more external transmitter devices to reapply the one or more AMF pulses to the foreign metallic implant after the predetermined delay period. In some embodiments, the control system is further configured to enable the one or more external transmitter devices to reapply the one or more AMF pulses to the foreign metallic implant when the one or more signals correspond to one or more acoustic emission signatures that indicate that a temperature of the foreign metallic implant is insufficient to disrupt the biofilm matrix on the surface of the foreign metallic implant. In some embodiments, the biofilm matrix is an extracellular polymeric substance (EPS) biofilm matrix on the surface of the foreign metallic implant. In some embodiments, the control system is further configured to determine that the one or more signals correspond to one or more acoustic emission signatures that indicate that the temperature of the foreign metallic implant is sufficient to reduce a number of bacteria on the surface of the foreign metallic implant.

In some embodiments, the one or more external transmitter devices may be one or more of a solenoid coil, a saddle coil, a pancake coil, and a phased array. In some embodiments, the one or more external acoustic sensor devices may be further configured to detect one or more acoustic waves emitted from soft tissue adjacent to the implant when heated to a particular temperature threshold. In some embodiments, the temperature threshold may approach 100° C. while in other embodiments, the temperature threshold may approach 60° C. In some embodiments, the one or more acoustic waves may begin to be detected at temperatures of approximately 60° C. and may continue to be detected at temperatures between 60° C. and 100° C. In some embodiments, the one or more external acoustic sensor devices may be further configured to detect one or more acoustic waves having a frequency between 500 Hz and 1000 Hz. In some embodiments, one or more acoustic waves at other frequencies may be detected. In some embodiments, the control system may be further configured to receive one or more signals associated with a temperature from the one or more external acoustic sensor devices, and adjust at least one of a duration, frequency, and amplitude of the one or more AMF pulses based on the one or more signals to maintain the surface of the foreign metallic implant at a desired temperature for a specific time period.

In some embodiments, the system may further include one or more internal temperature sensors embedded into the surface of the foreign metallic implant, the one or more internal temperature sensors configured to measure the temperature of the surface of the foreign metallic implant and output one or more output signals. In some embodiments, the system may further include one or more external optical receiver devices configured to detect photons emitted from one or more thermoluminescent materials embedded into the surface of the foreign metallic implant, the one or more thermoluminescent materials configured to emit the photons upon sensing a temperature greater than a predetermined threshold on the surface of the foreign metallic implant. In some embodiments, the control system may be further configured to receive one or more shut off signals from the one or more external optical receiver devices when photons are detected, and enable the one or more external transmitter devices to shut off upon receipt of the one or more shut off signals. In some embodiments, the control system may be further configured to receive one or more signals associated with a temperature from the one or more internal temperature sensors, and adjust a duration of the one or more AMF pulses based on the one or more signals to maintain the surface of the foreign metallic implant at a desired temperature for a specific time period.

In some embodiments, a foreign metallic implant treatment apparatus includes a housing and a plurality of AMF transmitters configured to apply one or more AMF pulses to the foreign metallic implant in three orthogonal directions. In some embodiments, the plurality of AMF transmitters are configured as pairs situated on opposing sides of the metallic implant in each of a Cartesian x-direction, y-direction, and z-direction. In some embodiments, each of the AMF transmitters in a pair are situated in parallel planes from each other. In some embodiments, at least one of the plurality of AMF transmitter pairs is configured to rotate about a longitudinal axis of the foreign metallic implant and apply the one or more AMF pulses at different positions around the longitudinal axis. In some embodiments, at least one of the plurality of AMF transmitter pairs is configured to rotate about one or more rotational axes other than a longitudinal axis of the foreign metallic implant and apply the one or more AMF pulses at different positions around the one or more rotational axes. In some embodiments, the plurality of AMF transmitters are configured to apply one or more AMF pulses to the foreign metallic implant in the three orthogonal directions simultaneously. In some embodiments, the plurality of AMF transmitter pairs are in a fixed position configured to enable a position of the foreign metallic implant to change between the plurality of AMF transmitter pairs. In some embodiments, the plurality of AMF transmitter pairs are in a fixed position configured to enable the foreign metallic implant to rotate between the plurality of AMF transmitter pairs. In some embodiments, the apparatus further includes one or more ferromagnetic materials configured to be movable around the foreign metallic implant. In some embodiments, the one or more ferromagnetic materials are configured to shape the one or more AMF pulses and modify an AMF distribution around the foreign metallic implant.

In some embodiments, a method of treating and preventing bacterial biofilms on a foreign metallic implant includes enabling, by a control system having at least one processor, one or more external transmitter devices including an AMF transmitter to apply one or more AMF pulses to the foreign metallic implant for one or more of a predetermined time period, pulse duration, pulse repetition frequency, and at a predetermined power level; receiving, by the control system, one or more signals from one or more external acoustic sensor devices configured to receive one or more acoustic emission signatures from tissue located in a vicinity of the foreign metallic implant; determining, by the control system, that the one or more signals correspond to one or more acoustic emission signatures that indicate that a temperature of the foreign metallic implant is sufficient to disrupt a biofilm matrix on a surface of the foreign metallic implant; and enabling one or more antibiotic or antimicrobial treatments to be applied to the foreign metallic implant.

In some embodiments, the method further includes enabling, by the control system, the one or more external transmitter devices to shut off for a predetermined delay period after applying the one or more AMF pulses. In some embodiments, the method further includes enabling, by the control system, the one or more external transmitter devices to reapply the one or more AMF pulses to the foreign metallic implant after the predetermined delay period. In some embodiments, the method further includes enabling the one or more external transmitter devices to reapply the one or more AMF pulses to the foreign metallic implant when the one or more signals correspond to one or more acoustic emission signatures that indicate that a temperature of the foreign metallic implant is insufficient to disrupt the biofilm matrix on the surface of the foreign metallic implant. In some embodiments, the biofilm matrix is an extracellular polymeric substance (EPS) biofilm matrix on the surface of the foreign metallic implant. In some embodiments, the method further includes determining that the one or more signals correspond to one or more acoustic emission signatures that indicate that the temperature of the foreign metallic implant is sufficient to reduce a number of bacteria on the surface of the foreign metallic implant.

In some embodiments, the method further includes enabling, by the control system, the one or more external transmitter devices to shut off for a predetermined delay period after applying the one or more AMF pulses. In some embodiments, the method further includes enabling, by the control system, the one or more external transmitter devices to reapply the one or more AMF pulses to the foreign metallic implant after the predetermined delay period. In some embodiments, the method further includes enabling the one or more external transmitter devices to reapply the one or more AMF pulses to the foreign metallic implant when the one or more signals correspond to one or more acoustic emission signatures that indicate that a temperature of the foreign metallic implant is insufficient to disrupt the biofilm matrix on the surface of the foreign metallic implant. In some embodiments, the method further includes determining that the one or more signals correspond to one or more acoustic emission signatures that indicate that the temperature of the foreign metallic implant is sufficient to reduce a number of bacteria on the surface of the foreign metallic implant. In some embodiments, the method further includes receiving, by the control system, one or more signals associated with a temperature from the one or more external acoustic sensor devices; and enabling, by the control system, an adjusting of at least one of a duration, frequency, and an amplitude of the one or more AMF pulses based on the one or more signals to maintain the surface of the foreign metallic implant at a desired temperature for a specific time period.

In some embodiments, the method further includes enabling, by the control system, one or more internal temperature sensors embedded into the surface of the foreign metallic implant to measure the temperature of the surface of the foreign metallic implant and output one or more output signals. In some embodiments, the method further includes enabling, by the control system, one or more external optical receiver devices to detect photons emitted from one or more thermoluminescent materials embedded into the surface of the foreign metallic implant, the one or more thermoluminescent materials configured to emit the photons upon sensing a temperature greater than a predetermined threshold on the surface of the foreign metallic implant. In some embodiments, the method further includes enabling, by the control system, one or more external optical receiver devices to detect the photons, receiving, by the control system, one or more signals from the one or more external optical receiver devices when photons are detected; and enabling, by the control system, the one or more external transmitter devices to shut off upon receipt of the one or more signals.

In some embodiments, the method further includes receiving, by the control system, one or more signals associated with a temperature from the one or more internal temperature sensors; and enabling, by the control system, the adjusting of a duration of the one or more AMF pulses based on the one or more signals to maintain the surface of the foreign metallic implant at a desired temperature for a specific time period.

In some embodiments, a system is configured to apply one or more AMF pulses for one or more of a predetermined time period, a predetermined pulse duration, a predetermined pulse repetition frequency, and at a predetermined power level. In some embodiments, the one or more AMF pulses are applied by one or more AMF transmitters. In some embodiments, the one or more AMF pulses are sufficient to create one or more acoustic emission signatures from tissue. In some embodiments, the system is configured to detect one or more signals corresponding to the one or more acoustic emission signatures. In some embodiments, the one or more acoustic emission signatures are detected by one or more acoustic sensor devices. In some embodiments, the system may determine that one or more antibiotic or antimicrobial treatments are appropriate. In some embodiments, the system may determine that one or more antibiotic or antimicrobial treatments are appropriate when the one or more acoustic emission signatures are detected.

The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system, or a component of a system, that "comprises," "has," "includes" or "contains" one or more elements or features possesses those one or more elements or features, but is not limited to possessing only those elements or features. Likewise, a method that "comprises," "has," "includes" or "contains" one or more steps possesses those one or more steps, but is not limited to possessing only those one or more steps. Additionally, terms such as "first" and "second" are used only to differentiate structures or features, and not to limit the different structures or features to a particular order.

Any embodiment of any of the disclosed methods, systems, system components, or method steps can consist of or consist essentially of—rather than comprise/include/contain/have—any of the described elements, steps, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

The foregoing has outlined rather broadly certain features and technical advantages of embodiments of the present invention in order that the detailed description that follows may be better understood. Additional features and advantages will be described below. It should be appreciated by those having ordinary skill in the art that the conception and specific embodiments disclosed may be readily utilized as a basis for modifying and/or utilizing other structures for carrying out the same or similar purposes. It should also be realized by those having ordinary skill in the art that such equivalent constructions do not depart from the spirit and scope of the invention as set forth in the appended claims. Additional features will be better understood from the following description when considered in connection with the accompanying figures. It is to be expressly understood, however, that each of the figures is provided for the purpose of illustration and description only and is not intended to limit the present invention.

BRIEF DESCRIPTION OF THE DRAWINGS

The following drawings illustrate by way of example and not limitation. For the sake of brevity and clarity, every feature of a given method or system is not always labeled in every figure related to that method or system. Identical reference numbers do not necessarily indicate an identical feature. Rather, the same reference number may be used to indicate a similar feature or a feature with similar functionality, as may non-identical reference numbers.

DETAILED DESCRIPTION OF ILLUSTRATIVE EMBODIMENTS

Figure 1:
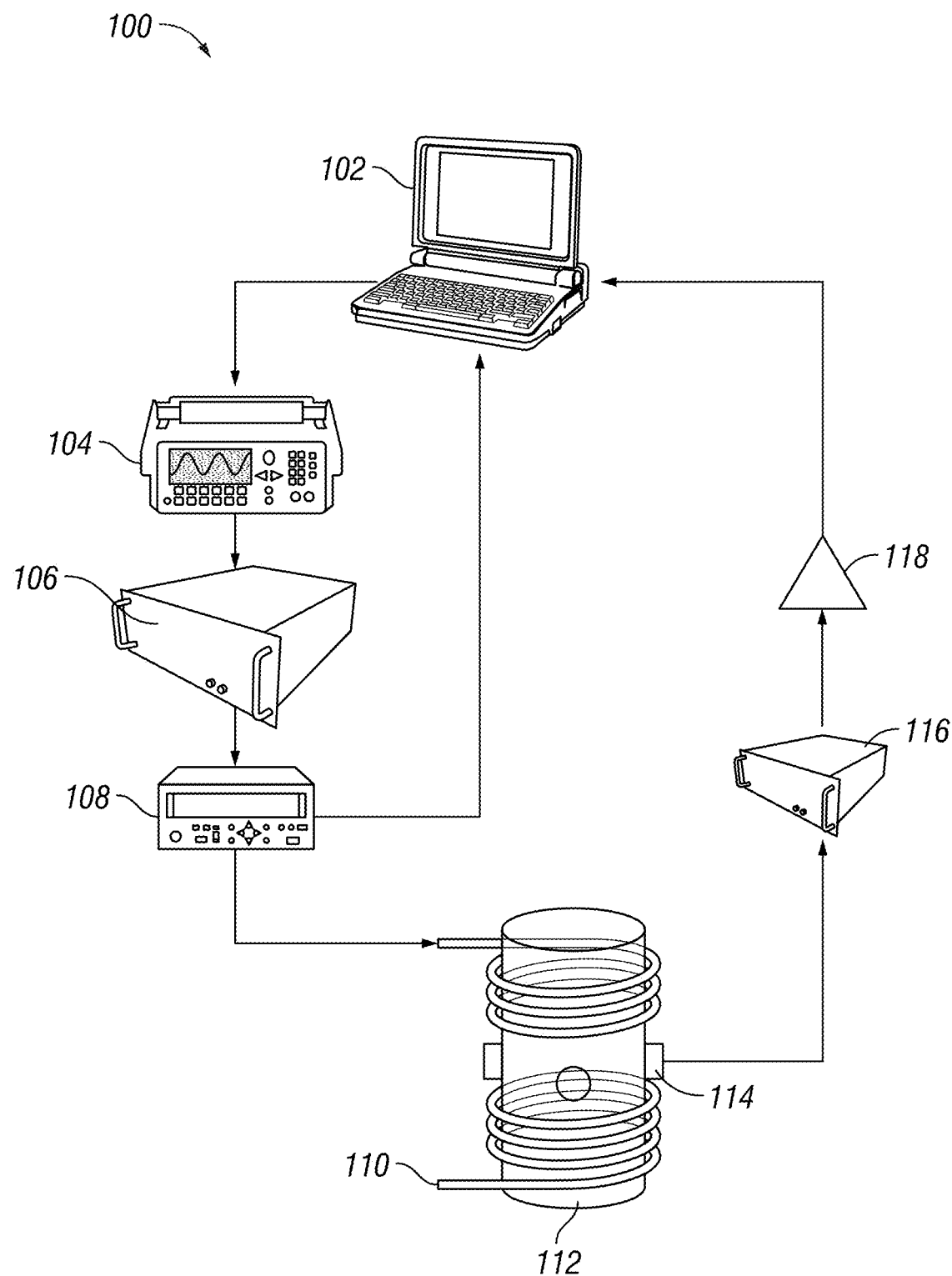
FIG. 1 depicts an exemplary control feedback system for applying inductive heating to foreign metallic implants according to an embodiment of the disclosure.

The embodiments discussed below describe systems, apparatus, and methods for the treatment of biofilms located on the surface of foreign metallic implants inside the body. In some embodiments, foreign metallic implants may include prosthetic joints, various prosthetic implants such as pins, screws, rods, clamps, or foreign objects such as shrapnel. In some embodiments, the method may involve the use of an alternating magnetic field (AMF) generated from a conductor located outside the body such that sufficient magnetic flux passes through the implant within the body to generate one or more superficial eddy currents on the surface of the implant. In some embodiments, the implant may be ferromagnetic. In these cases, additional heating due to magnetic hysteresis may also occur. In the embodiments described, the implant may have an electrical conductivity that permits one or more superficial eddy currents, as may be typically encountered in metal implants. The heating produced by direct eddy current heating may achieve uniform heating across the implant. In at least some of the embodiments described, the power, frequency, and timing of the AMF exposures may be controlled appropriately to achieve uniform heating of the surface of the implants in as rapid a manner as possible under existing circumstances and technology. In order to accomplish uniform heating of the implant while providing safety precautions to avoid damage to the surrounding tissue, a pulsed AMF exposure with appropriate delays may be applied from multiple AMF transmitters suitably arranged around the target implant. This process may be continued until a bacterial biofilm that may be present across the surface of an infected implant is weakened and/or eradicated to a desired extent.

The embodiments discussed below also describe systems, apparatus, and methods for measuring the heating of the implant. The present heating measurement techniques may help to ensure the safety of the tissue surrounding the implant and may signal the completion of a desired therapeutic effect such as partial or complete biofilm eradication. Tissue boiling can occur on a surface of the implant when the temperature approaches or exceeds 100° C. However, small bubbles may form in heated tissue at temperatures below this threshold (e.g., between 60° C. and 80° C.). The formation and collapse of these bubbles may emit acoustic energy that travels outside the body and can be measured almost instantaneously by various types of acoustic sensors, including both external and internal acoustic sensors. In some embodiments, one or more remote acoustic sensors can be integrated into the AMF delivery system to modulate the amplitude, pulse duration or pulse repetition frequency of the AMF pulses, or turn off power if acoustic energy is detected. Because these acoustic emissions may manifest themselves at temperatures below tissue boiling, this process may comprise a feedback regulation of the AMF heating process that may prevent the surface implant temperature from reaching the temperature threshold for tissue boiling. In some embodiments, one or more materials may be embedded into the metallic implants that may utilize a thermoluminescence principle. The material or these materials may exhibit a temperature dependent fluorescence and may emit photons once a particular temperature threshold is reached. An optical detector or receiver may be used to receive the emitted photons and may determine whether a specific temperature threshold is exceeded.

Embodiments described in this disclosure are suited for treating at least some biofilms because cells may exhibit sensitivity to elevated temperatures in a time and temperature dependent manner. For example, eukaryotic cells may have the ability to tolerate moderate temperature elevations through the expression of heat-shock proteins, and can withstand temperatures up to 41-42° C. for some duration. However, once temperatures become greater than 43° C., cells may die at an increasing rate. At temperatures greater than 54-55° C., greater than 3-4 logs of cell death may be achieved within a few seconds. Therefore, extended exposures at lower temperatures or shorter exposures at high temperatures may be sufficient to directly kill bacteria located on the surface of a metal implant. In addition to directly killing cells, heat may also weaken or remove portions of the biofilm matrix itself, which may increase the efficacy and/or penetration of antimicrobial agents, which may normally be restricted in their access to microbes that nest in the biofilm. Therefore, when one combines the embodiments described with an antimicrobial regimen (e.g., antibiotics), the impact of heat on the biofilm and/or the bacteria may augment the effect of a given dose of antibiotic, or may lower the dose required to achieve sterilization of an infected implant. Embodiments of the present treatment methods for bacterial biofilms can be combined with locally or systemically administered chemical agents to treat regional or systemic components of the infection, such as antibiotics, or temperature-sensitive compounds.

Referring now to the drawings, FIG. 1 depicts an exemplary control feedback system 100 for applying inductive heating to a foreign metallic implant according to an embodiment of the disclosure. In the embodiment shown, a desired treatment regimen may be selected and controlled by one or more control computers 102. The control computer 102 may be capable of transmitting control signals via one or more function generators 104, one or more amplifiers 106, and one or more power meters 108 to one or more AMF transmitters 110 to control characteristics such as power, duty cycle, frequency, pulse duration, and pulse repetition frequency, among others. In the embodiment shown of control system 100, the control computer 102 may also be capable of receiving and processing acoustic emissions from the implant or tissue in its immediate vicinity through one or more remote acoustic sensors 114 to determine information such as acoustic information. In some embodiments, the control computer 102, the information may be representative of temperature information or may be other types of information. In some embodiments, the one or more signals from the one or more remote acoustic sensors 114 may comprise one or more signals that may indicate that one or more acoustic emission signatures may be greater than a predetermined threshold. In some embodiments, the signals from the one or more remote acoustic sensors 114 may comprise signals that may indicate that one or more acoustic emission signatures may be less than a predetermined threshold. In some embodiments, the predetermined threshold may be an acoustic emission signature amplitude threshold. In some embodiments, the control computer 102 may include a display to provide information about the progress of treatment to a user, as well as various input elements that may enable the user to interact with the control computer 102 and set desired parameters and/or adjustments. The control computer 102 may include standard components of a computer system such as a hard drive, monitor, printer, keyboard, mouse, among others, that may enable the user to interact with the control computer 102 and to record and/or reproduce data.

The control computer 102 may issue one or more commands or instructions to the function generator 104, which may produce a time varying electrical signal. The function generator 104 may have the ability to adjust the amplitude, frequency, phase offset, pulse duration and pulse repetition frequency of the time varying electrical signal. The function generator 104 may be controlled by the control computer 102 through elements such as a serial port, USB port, or Ethernet port, among others. In some embodiments, the function generator 104 may be directly integrated into the control computer 102. The time varying electrical signal may be amplified to a desired power level by the amplifier 106. In some embodiments, amplifier 106 may include a matching and tank circuit to achieve efficient power transfer and to tune the matching and tank circuit to a particular resonant frequency. The signal output by amplifier 106 may pass through the power meter 108, which may measure the forward and reflected power of the signal. This measurement data may be sent back to the control computer 102. The control computer 102 may use these measurements to adjust the levels of electrical power provided by the time varying electrical signal and/or monitor the efficiency of power transfer. If the control computer 102 adjusts the signal, it may issue an updated command to the function generator 104 to adjust the signal, which may then be transmitted through the amplifier 106 and power meter 108 for an updated measurement.

The signal emitted from the power meter 108 may be input into one or more AMF transmitters 110. In the embodiment shown, the AMF transmitter 110 may produce a time-varying magnetic field in a body area 112 to generate heating of the surface of a foreign metallic implant (not shown) located in the body area 112. One or more remote acoustic sensors 114 may be placed around the body area 112 being heated. In some embodiments, the one or more remote acoustic sensors 114 may be placed directly on the surface of skin covering the body area 112. The one or more remote acoustic sensors 114 may be placed at desired intervals around the body area 112 being heated. In some embodiments, the one or more remote acoustic sensors 114 may be placed at a distance above the body area 112. In some embodiments, the sensors may be temperature sensors, optical sensors, and/or wireless sensors. In some embodiments, the sensors may be removable sensors while in other embodiments, the sensors may be implanted in the body area 112 in various ways commonly known in the art. In the embodiment shown, acoustic sensors 114 may capture any acoustic emissions related to the boiling of tissue comprising the body area 112. The acoustic emissions may be converted to one or more signals by the acoustic sensors 114 and may be amplified by a pre-amplifier 116. The pre-amplifier 116 may transmit the one or more amplified signals to an analog-to-digital converter (ADC) 118, which may digitize the one or more amplified signals. In some embodiments, various types of data acquisition modules may be used. The one or more signals may then be input into and processed by the control computer 102 in order to determine whether adjustments to the time varying electrical signal are necessary.

In some embodiments, the control computer 102 may determine whether adjustments to the time varying electrical signal applied by the AMF transmitter 110 are necessary by measuring other properties of the control feedback system 100. In some embodiments, the control computer 102 may measure current delivered to the AMF transmitter 110. This measured current may represent total power delivered to the system 100. In some embodiments, the control computer 102 may measure a temperature increase in a cooling circuit that removes losses in the system electronics. This measurement may represent power lost from the system 100. A difference between the measured current and the measured temperature may represent the amount of power delivered to the implant. In some embodiments, knowledge of this quantity could be used to deliver a fixed number of pulses where power*time/pulse*#pulses=total energy (E) delivered to the implant. In some embodiments, knowing the specific heat capacity of the implant and assuming that the heat is uniformly distributed (this assumption can be accurate for low power exposures), the temperature elevation in the implant can be estimated as E/(density*volume*specific heat capacity). In some embodiments, the control computer 102 may measure the change in impedance when the implant is inserted into the AMF transmitter 110. This change in impedance can represent the "loading" that the implant presents to the system electronics and can be used to estimate the power delivered to the implant and thus the temperature elevation in the implant.

Figure 2:
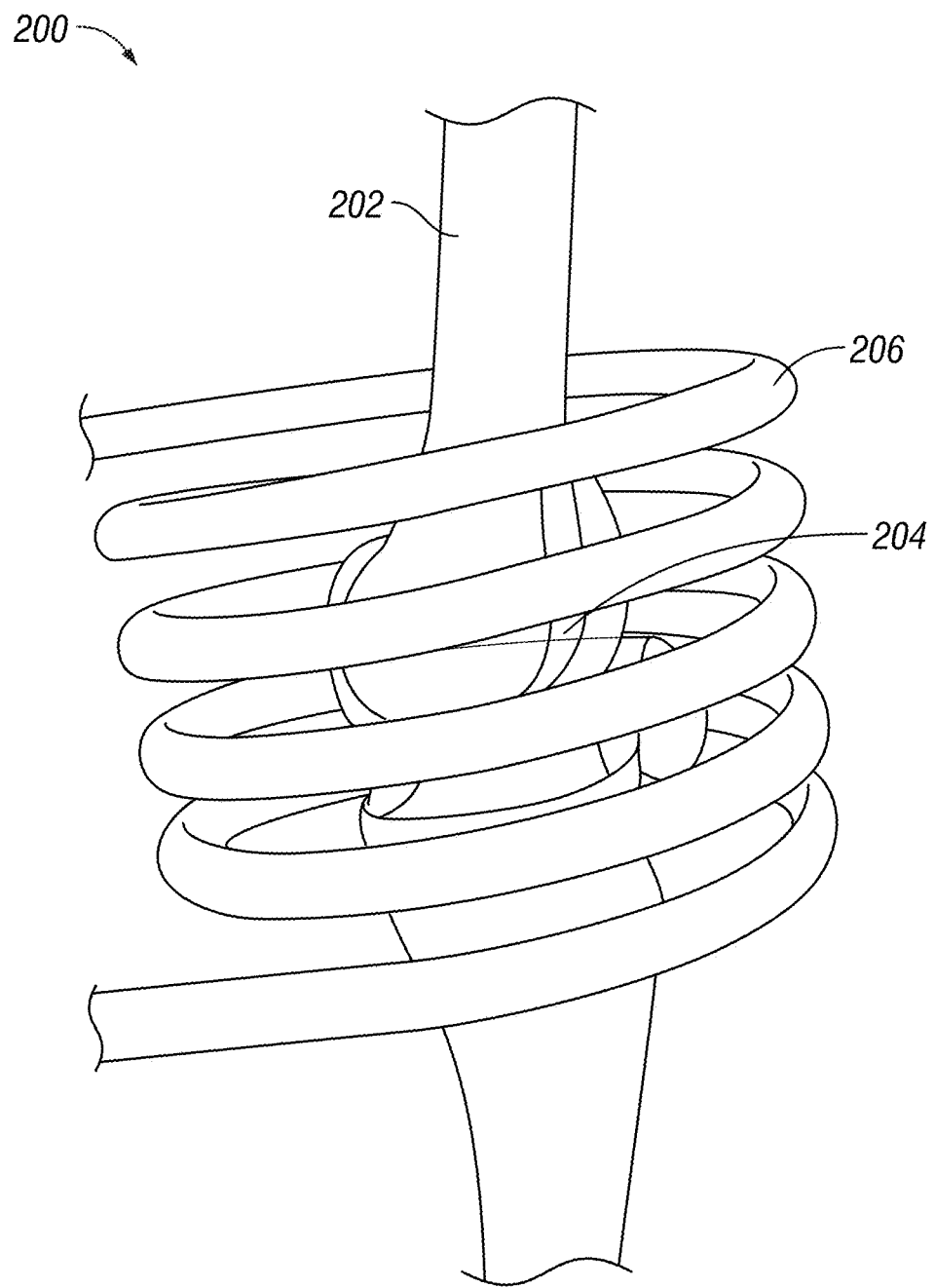
FIG. 2 depicts an exemplary AMF transmitter according to an embodiment of the disclosure.

FIG. 2 depicts an exemplary single coil AMF transmitter 200 according to an embodiment of the disclosure. A general type of transmitter can be some type of electrical conductor carrying a time-varying electrical signal located outside the body 202. In the embodiments shown, the AMF transmitter 200 may be able to create a time-varying magnetic field that crosses through a target metal implant 204 in the body. In the embodiment shown in FIG. 2, a transmitter may comprise a solenoid 206. Because a solenoid 206 may produce a uniform magnetic field along its inner axis, it may be suitable for exposing limbs and/or extremities to alternating magnetic fields. In other embodiments, a transmitter may comprise a saddle coil. A saddle coil may be placed around a hip to provide alternating magnetic fields for the treatment of implants in the pelvis. In other embodiments, multiple coils, a moving coil, and other types of AMF transmitters such as a pancake coil, among others, may be used to achieve a spatiotemporal variation of the alternating magnetic field.

The embodiments shown in FIGS. 1 and 2 may be adapted for different shapes and sizes of foreign metallic implants as well as those located both superficially and deeply within the body. However, a sufficient magnetic field strength should be experienced by the implant to generate enough current flow to produce a desired temperature elevation. This may be achieved through the type of transmitter located outside the body and may make it likely that a different shape of transmitter may be optimal for different anatomical targets. For example, the solenoid 206 may be well-suited for targeting objects within limbs and/or extremities, a saddle coil may be optimal for shoulders and hips, and an alternative type of AMF transmitter such as a pancake coil may be optimal for abdominal and/or vertebral targets.

Any foreign metallic implant comprised of conductive material may respond to the alternating magnetic field with a temperature elevation. The magnitude of the temperature elevation may be related to the electrical conductivity of the conductive material. Examples of metals compatible with the disclosed embodiments include metals commonly used in biomedical devices such as stainless steels, titanium, and platinum. However the rate of heating may vary slightly across different metals depending on their electrical conductivity, and system 100 may need to compensate for these differences. Alternatively, under the closed loop control exhibited by system 100, the treatment may continue to deliver power until a desired temperature is achieved. This characteristic may enable system 100 to be self-sufficient and less dependent on predetermined calibration for a particular metal.

Figure 3:
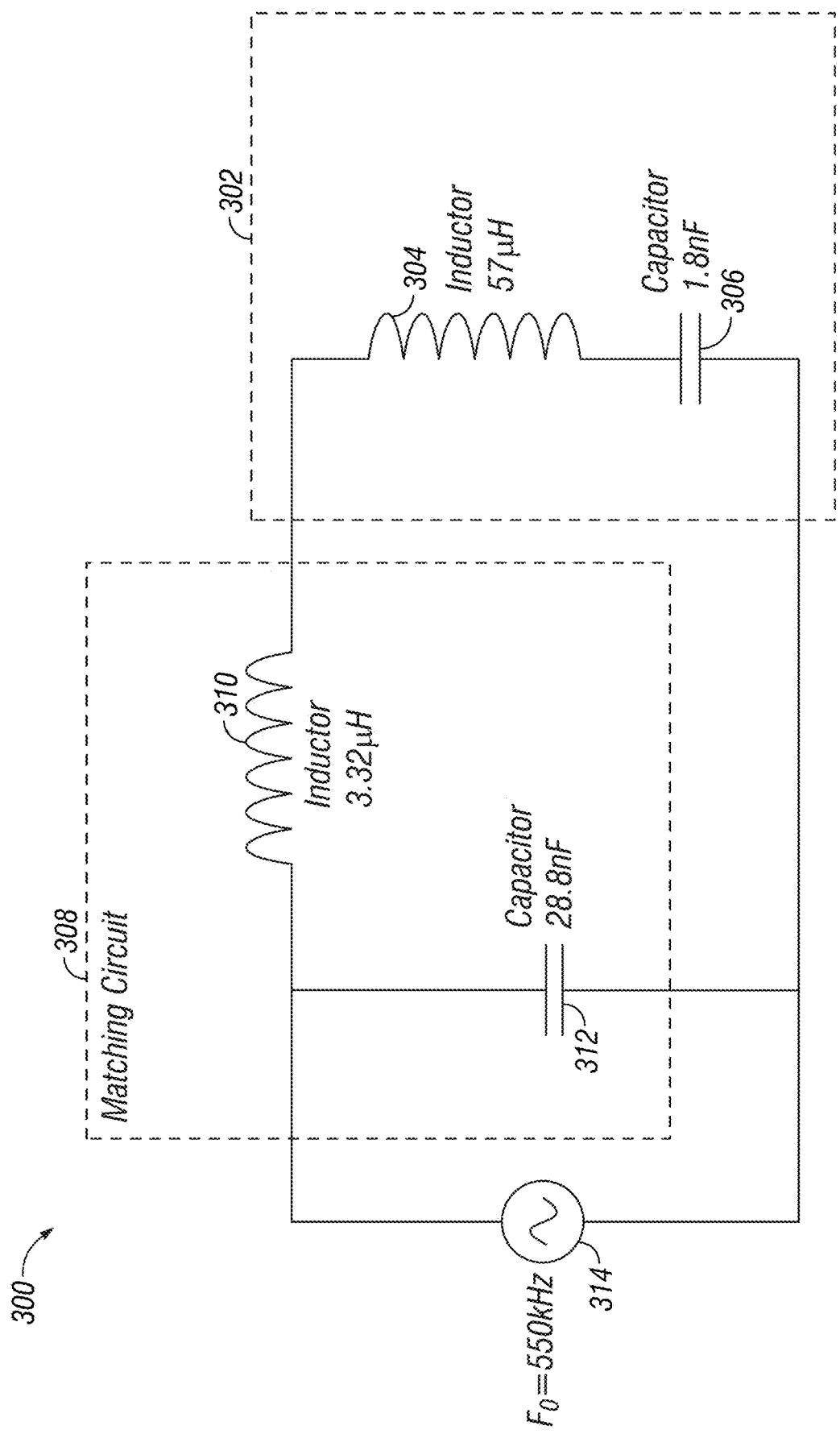
FIG. 3 depicts an electrical circuit representation of an exemplary AMF transmitter according to an embodiment of the disclosure.

FIG. 3 depicts an electrical circuit representation 300 of an exemplary AMF transmission circuit (such as transmitter 200) according to an embodiment of the disclosure. In the embodiment shown, a resonant or tank circuit 302 may include an inductor 304 and a capacitor 306 and may drive power efficiently through the AMF transmitter 200. In some embodiments, inductor 304 may comprise AMF transmitter 110 as shown in FIG. 1 or AMF transmitter 200 as shown in FIG. 2. The capacitor 306 may be placed in series (or parallel) with the inductor 304 to achieve a series or parallel resonant circuit having a frequency related to the numerical values of the inductor 304 and capacitor 306. In the embodiment shown, inductor 304 has an inductance of 57 μH and capacitor 306 has a capacitance of 1.8 nF but other suitable values may be used. In some embodiments, these values may be determined by a size and/or geometry of the AMF transmitter 110. These values may also be determined by a frequency of the frequency generator 104. In some embodiments, a matching circuit or transformer network 308 may be used to achieve impedance matching between the amplifier 106 and the tank circuit 302. In the embodiment shown, the matching circuit 308 may include an inductor 310 having an inductance of 3.32 μH and a capacitor 312 having a capacitance of 28.8 nF but other suitable values may be used. An oscillator 314 may also be used to provide a reference frequency for the tank circuit 302. In the embodiment shown, the oscillator 314 may provide a reference frequency of 550 kHz but other suitable values may be used. In some embodiments, oscillator 314 may comprise the frequency generator 104 and amplifier 106 as shown in FIG. 1.

Figure 4:
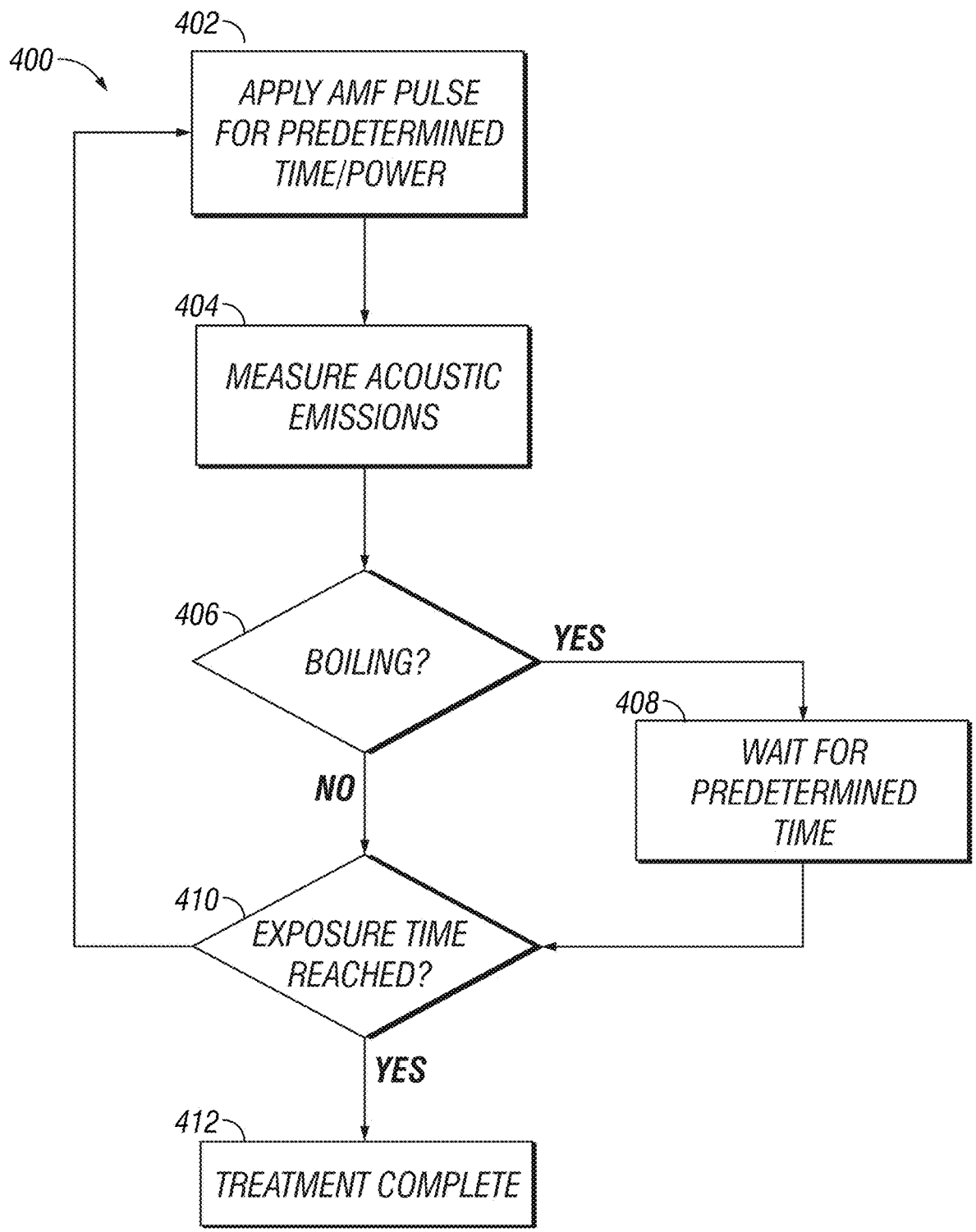
FIG. 4 depicts an exemplary method of applying inductive heating to foreign metallic implants according to an embodiment of the disclosure.

FIG. 4 depicts an exemplary method 400 of applying inductive heating to foreign metallic implants according to an embodiment of the disclosure. In one embodiment of the disclosure, method 400 may be implemented by system 100. As shown in FIGS. 1 and 2, inductive heating may be achieved by enabling an alternating magnetic field to pass through a conductor (e.g., foreign metallic implant) and induce an electrical current on the surface of the conductor. This current may be subject to resistive losses based on the electrical properties of the metal. These resistive losses may then be converted to heat. Inductive heating of a foreign metallic implant may be completely non-contact and can be generated from outside the body. Inductive heating may also achieve good energy transfer from the AMF transmitter to the metal conductor, which may enable high temperatures to be achieved in a short time period. The currents generated on the metal conductor may be restricted to the outer surface due to a phenomenon called the skin effect. The skin effect may enable the heating to have cytotoxic effects on biofilms or infections occurring at the surface of the metal. In some embodiments, these cytotoxic effects may comprise a weakening or eradication of the biofilm or infection.

In the embodiment shown in FIG. 4, method 400 may begin at step 402 by applying an AMF pulse to a foreign metallic implant for one or more of a predetermined time, pulse duration, pulse repetition frequency, and at a predetermined power. In some embodiments, a time-varying magnetic field may be achieved by transmitting a time-varying electrical current through the one or more AMF transmitters 110 that may be located outside the body 112. As shown in FIG. 1, this may be implemented by a signal source such as function generator 104 and a suitable amplifier 106 to generate a time-varying signal of sufficient power. In some embodiments, the range of powers that might be suitable for this application may vary from a few Watts for a small implant close to the AMF transmitter to up to 10 kW for a deep-seated large object. In some embodiments, the frequency range for transmission can also vary across a large range, but may typically be above the threshold for peripheral nerve stimulation (~100 kHz) and below the threshold where tissue heating becomes significant (>10-20 MHz).

As discussed above, a characteristic of inductive heating of metal implants may be the restriction of one or more induced eddy currents to the outer surface of the foreign metal implant due to an effect known as the skin effect. In one example, for a typical metal exposed to an alternating magnetic field of 500 kHz, the skin effect may result in a bulk of the current flow existing within 0.2-0.5 mm from the surface of the metal. Therefore, superficial heating may be achieved, which may be desirable for targeting molecules located on the surface of the foreign metallic implant such as bacteria and biofilms. In some embodiments, the duration of AMF exposure can also vary, and may be related to the desired temperature elevation on the implant and the duration required to achieve a target cytotoxic effect on a biofilm.

Another characteristic of the induced current distribution (and hence the induced temperature distribution) on the surface of the metal implant may be that the current distribution is relatively heterogeneous. This may result in one or more eddy currents following preferred paths along the surface of the implant. As a result, the initial AMF pulse may induce heating that is quite non-uniform. In some embodiments, the AMF pulse can be continuous or may be applied intermittently. Intermittent pulsed exposures may have the benefit of allowing for thermal conduction and equalization of the temperatures on the surface of the metal implant during pauses between exposures. Therefore, pulsed exposures may achieve a uniform temperature distribution across the surface of the metal implant that may result in a desired heating level for treating target cells, bacteria, and/or biofilms. In embodiments using multiple AMF transmitters, the multiple AMF transmitters can be operated independently or as a phased array to achieve additional spatial control over the one or more induced electric and magnetic fields to distribute heating across the surface of the implant. Alternatively, mechanical motion can be employed to achieve the same effect.

As discussed above, in some embodiments, the duration of the one or more AMF pulses may be for a predetermined time suitable for enabling a uniform heating of the surface of the metal implant. As the metal implant receives more pulses from the AMF transmitter, its surface temperature may rise gradually. Additionally, the power intensity of the AMF pulses may be adjusted by the feedback control system 100 shown in FIG. 1. As the surface temperature of the implant approaches tissue boiling temperature, the pulse duration may become shorter and/or the power intensity of each pulse may decrease.

An important aspect of using induction heating to generate temperature elevations on the surface of metal implants may be preventing temperature elevations that may cause excessive damage to surrounding normal tissues. Therefore, it may be desirable to have some form of temperature feedback during heating that may be incorporated into one or more control signals or shut off signals. In the embodiment shown, method 400 may enable a type of temperature feedback at step 404 by monitoring one or more acoustic emissions from tissue in the vicinity of the implant. As the temperature on the surface of the implant approaches the boiling point of water, microbubbles may start to form in the tissue. The formation and collapse of these microbubbles may exhibit a very distinctive acoustic signature and may begin to exhibit themselves at temperatures between approximately 60° and 80° C. This acoustic signature may travel outwards from the site of occurrence and can be detected outside the body 112 with one or more suitably placed acoustic sensors 114 as shown in FIG. 1. The time to detect these emissions from their onset may be on the order of microseconds. In the embodiment shown, the detection of these acoustic signatures can be used as a safety shutoff to ensure that temperatures on the surface of the implant remain below the temperature threshold of tissue boiling. In some embodiments, acoustic signatures may exist in a frequency range between 500 and 1000 Hz and may be reliably detected by the one or more acoustic sensors 114 when temperatures approach boiling on the surface of the metal implant. In some embodiments, acoustic signatures may be detected when soft tissue is heated to a temperature between approximately 60° and 80° C. Other frequency ranges may exist that can be exploited and monitored. The one or more acoustic sensors 114 may also detect an amplitude of the acoustic signatures. This method of detection may be useful because it is inherently linked to a physical effect having a well-defined temperature. For example, as tissue temperatures approach boiling, the amplitude of the acoustic signatures may increase. Furthermore, transmission of the occurrence of the event to a control system 100 located outside the body may also occur inherently due to the nature of the resulting acoustic waves. In some embodiments, control system 100 may comprise one or more acoustic receivers or sensors. Therefore, no additional transmitters or other electronics may be required to be implanted inside the body. Therefore, system 100 implementing method 400 may be compatible with all types of existing metal implants without requiring any additional invasive modifications to the implants.

In addition to acoustic monitoring, another embodiment may directly detect temperature in or around the surface of the metal implant using one or more implanted temperature sensors. Such temperature sensors may be any type of sensor capable of detecting temperature (e.g., thermistors and thermocouples, among others.). In order to detect the temperature in the vicinity of the implant, the temperature sensors may be directly implanted into tissue percutaneously or through a catheter. In this embodiment, the temperature sensors may be substituted for acoustic sensors 114 and may detect the temperature of the surface of the implant directly. In this embodiment, step 404 may measure the temperature of the implant surface rather than measure acoustic emissions. The temperature sensors may then forward the information as a signal to pre-amplifier 116 and ADC 118 to be processed by control computer 102 as shown in FIG. 1. The control computer 102 may then control the duration and power of the applied AMF pulses in a similar way as discussed above.

In some embodiments, one or more thermoluminescent materials may be embedded on the implant surface at a point where surface temperature measurement may be desired. Thermoluminescent materials may emit photons once a specific temperature threshold is reached. As the surface temperature of the implant rises, higher numbers of photons may be emitted. In some embodiments, the one or more thermoluminescent materials may be pre-irradiated at the time of manufacture to ensure that photons are released upon reaching a particular temperature. These photons may be detected outside the body with one or more optical sensors. In this embodiment, the optical sensors may be substituted for acoustic sensors 114 and may detect the number of photons emitted from of the surface of the implant. The optical sensors may then forward the information as one or more signals to pre-amplifier 116 and ADC 118 to be processed by control computer 102 as shown in FIG. 1. The control computer 102 may then control the duration and power of the applied AMF pulses in a similar way as discussed above.

In the embodiment shown, method 400 may continue at step 406 with a determination by system 100 as to whether a threshold associated with tissue boiling is detected. This threshold may be the detection of one or more acoustic emissions associated with tissue boiling or the detection of a temperature approaching tissue boiling. If a tissue boiling threshold is detected, method 400 may continue at step 408 with system 100 stopping the AMF pulse and waiting for a predetermined time. During this predetermined time, the temperature of the metal implant surface may cool to a temperature lower than a temperature threshold associated with tissue boiling. This may provide the safety shutoff feature described above. Alternatively, if multiple AMF transmitters are employed, an AMF pulse can be delivered from a different transmitter once boiling is detected due to the AMF pulse from a first transmitter. If a tissue boiling threshold is not detected or if the predetermined wait time has been reached, method 400 may continue at step 408 with a determination by system 100 as to whether an implant surface exposure time has been reached. In some embodiments, the implant surface exposure time may be a time period predetermined by a user. This time period may correspond to a time period sufficient to weaken or eradicate bacteria or biofilms on the implant surface when the implant surface is maintained at a certain uniform surface temperature, depending on a desired treatment. In some embodiments, the implant surface exposure time may be a time period determined by control computer 102. This time period may be based on data received from sensors 114 and may be sufficient to maintain the implant surface at a certain uniform temperature long enough to weaken or eradicate bacteria or biofilms on the implant surface. In the embodiment shown, if the implant surface exposure time has not been reached, method 400 may continue at step 402. If the implant surface exposure time has been reached (i.e., an exposure time sufficient to weaken or eradicate bacteria or biofilm), method 400 may finish at step 412 and determine that the desired AMF pulse treatment of the implant is complete. In some embodiments, instead of proceeding directly to step 412, method 400 may enable a determination that the implant surface exposure time has been sufficient to disrupt a biofilm matrix. In some embodiments, this determination may be performed by receiving acoustic emissions that indicate that a temperature of the implant surface has reached a temperature adequate to weaken or eradicate a biofilm matrix. Upon a determination that this exposure time and/or this implant surface temperature has been reached, an antibacterial or antimicrobial treatment may be administered to the implant surface. Due to the weakening of the biofilm matrix, the effectiveness of the antimicrobial treatment may be increased. This may enable a lower dosage amount and/or a shortened treatment time.

Figure 5:
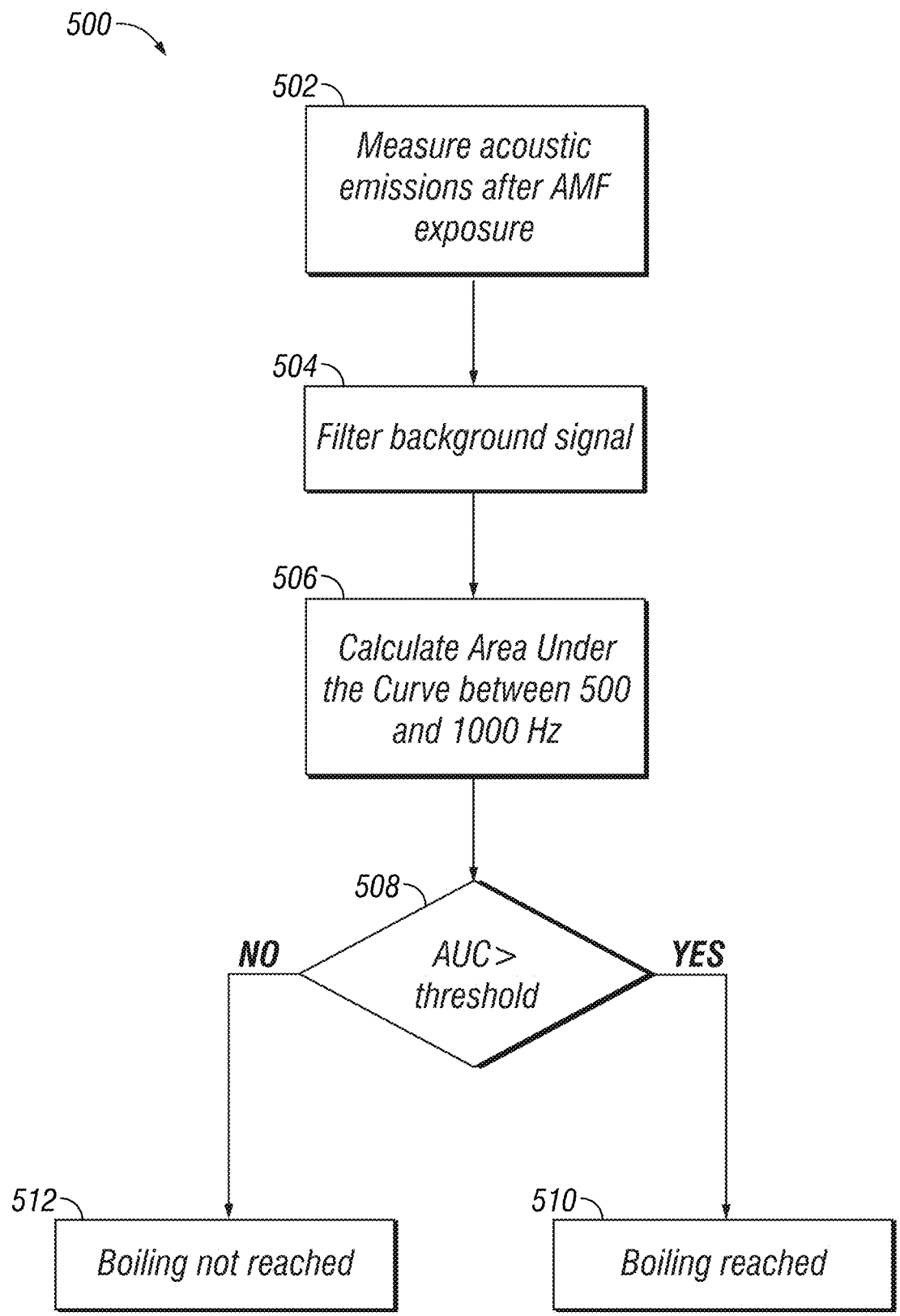
FIG. 5 depicts an exemplary method of measuring acoustic emissions from foreign metallic implants according to an embodiment of the disclosure.

FIG. 5 depicts an exemplary method 500 of measuring one or more acoustic emissions from foreign metallic implants according to an embodiment of the disclosure. In the embodiment shown, method 500 may be a more detailed embodiment of step 404 of method 400. At step 502, one or more acoustic sensors 114 may measure one or more acoustic emissions from the metallic implant and the surrounding tissues. At step 504 of method 500, pre-amplifier 116 and ADC 118 may filter one or more background signals from the acoustic emissions. At step 506 of method 500, control computer 102 may receive one or more filtered acoustic signals and may calculate an area under a temperature curve (AUC) between a particular frequency range. In the embodiment shown, the AUC may be calculated between a frequency range of 500 Hz and 1000 Hz. This AUC may correspond to the detected one or more filtered acoustic signals. At step 508 of method 500, control computer 102 may determine whether the AUC is greater or less than a temperature threshold associated with tissue boiling. If the AUC is greater than or equal to the temperature threshold, a threshold associated with tissue boiling has been reached 510 and method 400 may commence to step 408 discussed above. If the AUC is less than the temperature threshold, a threshold associated with tissue boiling has not been reached 512 and method 400 may commence to step 410 discussed above.

Figure 6:
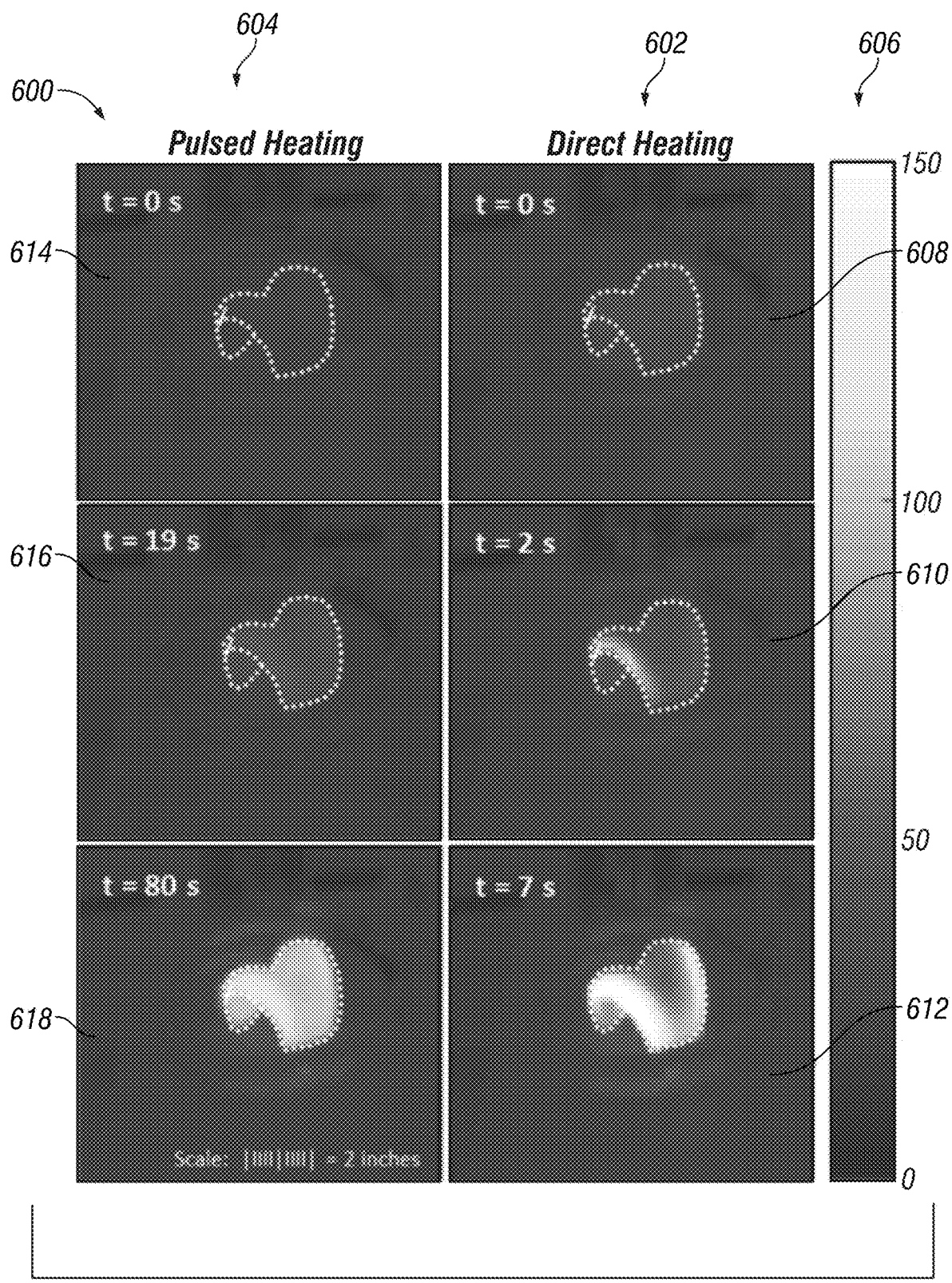
FIG. 6 depicts an infrared diagram illustrating temperature differences between continuous heating and pulsed heating according to an embodiment of the disclosure.

FIG. 6 depicts an exemplary infrared diagram 600 illustrating one or more temperature differences between direct continuous heating 602 and pulsed heating 604 according to an embodiment of the disclosure. In order to create infrared diagram 600, a discarded prosthetic metal knee implant was obtained and placed inside a solenoid AMF transmitter. An infrared camera was placed in the vicinity of the prosthetic implant such that the surface shown in the figure was visible. The implant was then exposed to AMF to generate continuous heating 602 and pulsed heating 604. Temperatures were recorded during these exposures to alternating magnetic fields with the thermal camera.

In the embodiment shown, the heating depicted in FIG. 6 may occur at step 402 of method 400 described above and may illustrate the skin effect. Diagram 600 also shows an infrared temperature scale 606 depicting a temperature corresponding to a particular infrared intensity on the surface of an implant. In the embodiment shown, continuous heating 602 may achieve rapid but non-uniform temperature elevations along the surface of a metal implant. As can be seen in diagram 600, temperatures >150° C. can be observed within a short time period that may be unsafe and result in damage to surrounding tissue. In photo 608, no heating is observed at a time of 0 seconds. After being subjected to continuous heating 602 for a time of 2 seconds, photo 610 shows that the temperature of an edge of the implant has already reached a temperature close to or exceeding 100° C., which may result in tissue boiling. However, photo 610 also shows that a majority of the implant surface may have a temperature <50° C. This temperature may not be adequate to have a desired effect on bacteria or a biofilm on the implant surface. Therefore, in photo 610, a portion of the implant has reached an unsafe temperature and a majority of the implant has not reached a desired biofilm treatment temperature in the short time span of 2 seconds. After being subjected to continuous heating 602 for a time of 7 seconds, photo 512 shows that the temperature of the implant edges has reached a temperature >150° C. while the middle of the implant still has not reached a desired treatment temperature. Therefore, continuous heating 602 may not be a preferred method to implement method 400. In contrast, pulsed heating 604 may result in a slower and more uniform temperature elevation across the entire surface of the implant. In photo 614, similar to photo 608, no heating is observed at a time of 0 seconds. However, in photo 616, the implant surface has a uniform temperature that poses no threat of tissue boiling even after a time of 19 seconds of pulsed heating 604. In photo 618, the implant has reached a temperature >150° C. after being subjected to pulsed heating 604 for a time period of 80 seconds. However, photo 618 shows that the temperature is uniform across the surface of the implant. While the safety mechanisms described above would turn off the AMF pulse when the temperature approached tissue boiling temperature, it can be seen that pulsed heating 604 may provide an effective way to uniformly heat the implant surface to a temperature adequate to have a desired effect on bacteria or biofilms on the implant surface. Therefore, pulsed heating 604 may provide a preferred method of implementing method 400 described above.

Figure 7:
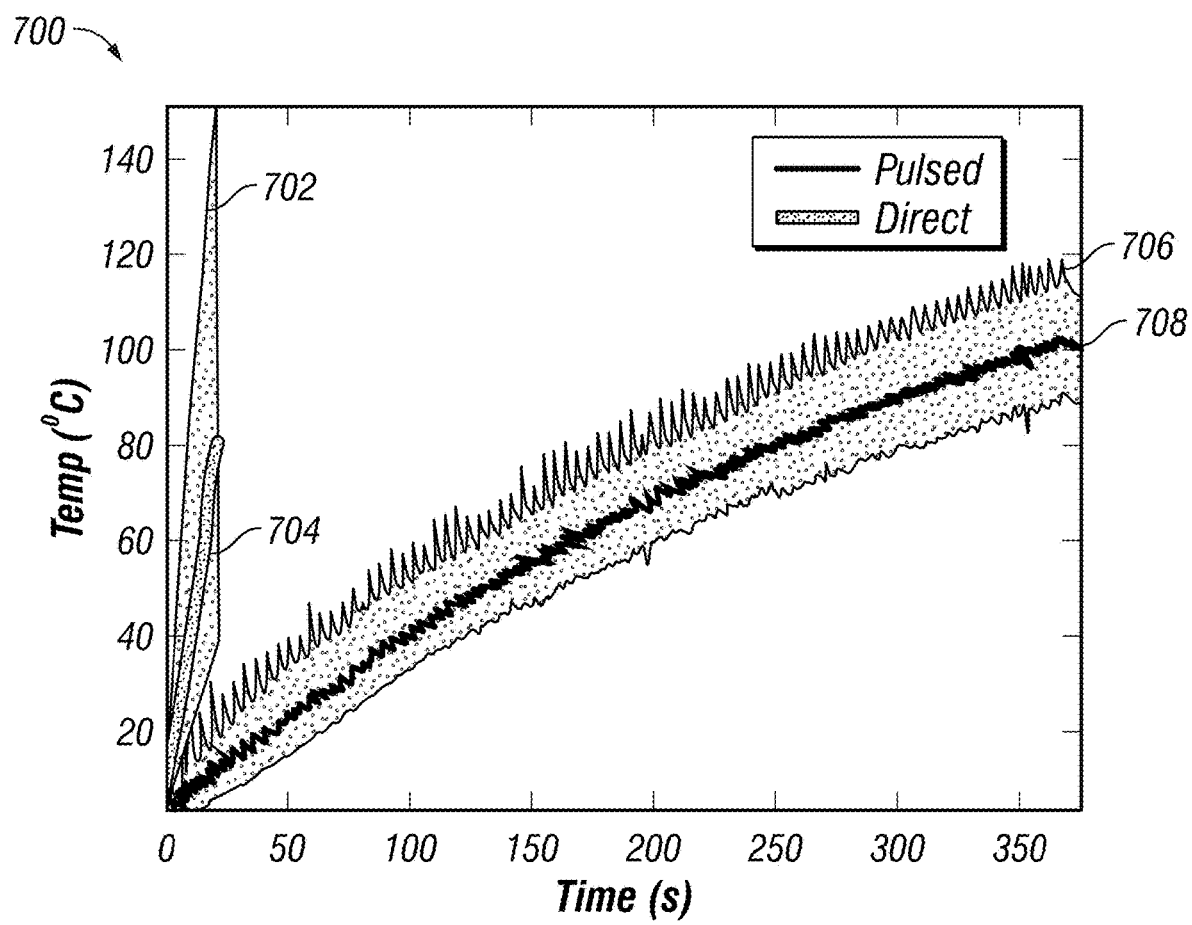
FIG. 7 depicts a graph illustrating temperature differences between continuous heating and pulsed heating according to an embodiment of the disclosure.

FIG. 7 depicts a graph 700 illustrating temperature differences between continuous heating and pulsed heating shown by the images shown in FIG. 6. The graph 700 shows a distribution of surface temperatures measured with infrared thermometry during exposures of a metal implant to both continuous and pulsed alternating magnetic fields. Similar to diagram 600, the graph 700 shows how continuous AMF exposures 702 may achieve rapid but non-uniform heating and may quickly cause an implant to have a high surface temperature. For example, in the embodiment shown, the continuous heating temperature 704 has risen to approximately 80° C. in a time period of <20 seconds, but has a variation of over 100° C. across the surface of the implant. However, in the case of pulsed AMF exposures 706, a more gradual heating may be achieved with a greater temperature uniformity across the surface of the implant. For example, in the embodiment shown, the pulsed heating temperature 708 does not reach approximately 80° C. until a time period of approximately 250 seconds. Also, as shown in FIG. 7, the uniformity of pulsed heating temperature 708 on the implant surface is much improved over the uniformity of continuous heating temperature 704, with a variation of approximately 20° C. across the surface.

Figure 8:
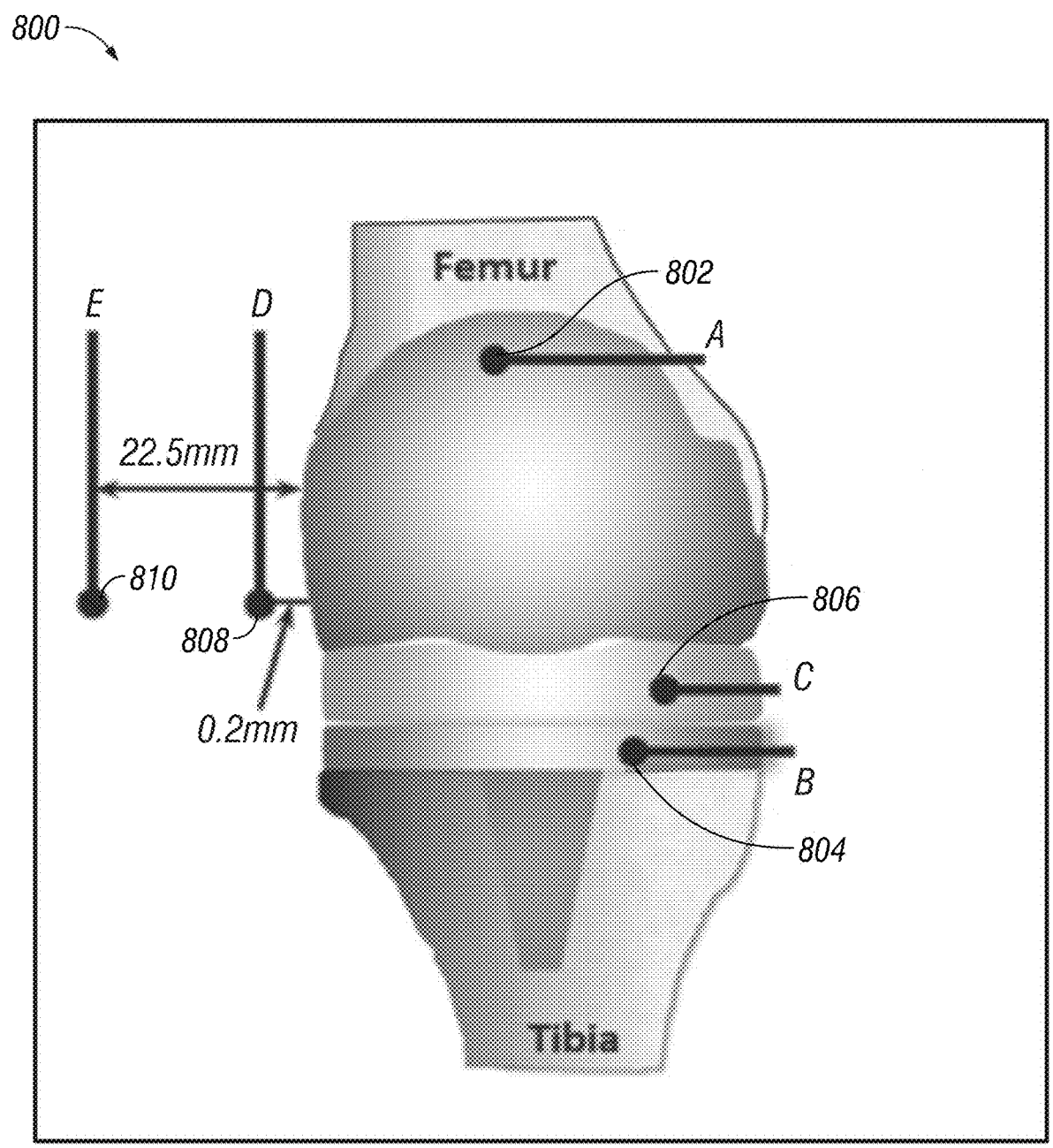
FIG. 8 depicts an exemplary prosthetic joint that may be heated according to an embodiment of the disclosure.

FIG. 8 depicts an exemplary prosthetic knee joint 800 that may be heated according to an embodiment of the disclosure. In these measurements, a discarded knee implant was attached to a bone and then suspended in a gel matrix to create a phantom leg for testing the feasibility of achieving therapeutic temperatures on a full-scale knee implant. In the embodiment shown, one or more temperature measurements were taken on a primary joint area 802, a secondary joint area 804, a plastic spacer 806, a close tissue area 808, and a far tissue area 810. In the embodiment shown, close tissue area 808 is approximately 2 mm from the prosthetic knee joint 800 and far tissue area 810 is approximately 22 mm from the prosthetic knee joint 800. In the example embodiment shown, implanted fiber optic sensors were used to measure the temperature elevation at different areas 802, 804, 806, 808, and 810 in and around prosthetic knee joint 800 after exposure to one or more pulsed alternating magnetic fields at 200 KHz frequency. In the embodiment shown, the pulses were 300 ms in duration and applied every 15 seconds. In the embodiment shown, areas 802 and 804 comprise metal, area 806 comprises plastic, and areas 808 and 810 comprise human tissue. Therefore, because metal, plastic, and tissue each have different electrical and thermal conductivities, each material may exhibit different heating patterns when exposed to the alternative magnetic fields.

Figure 9:
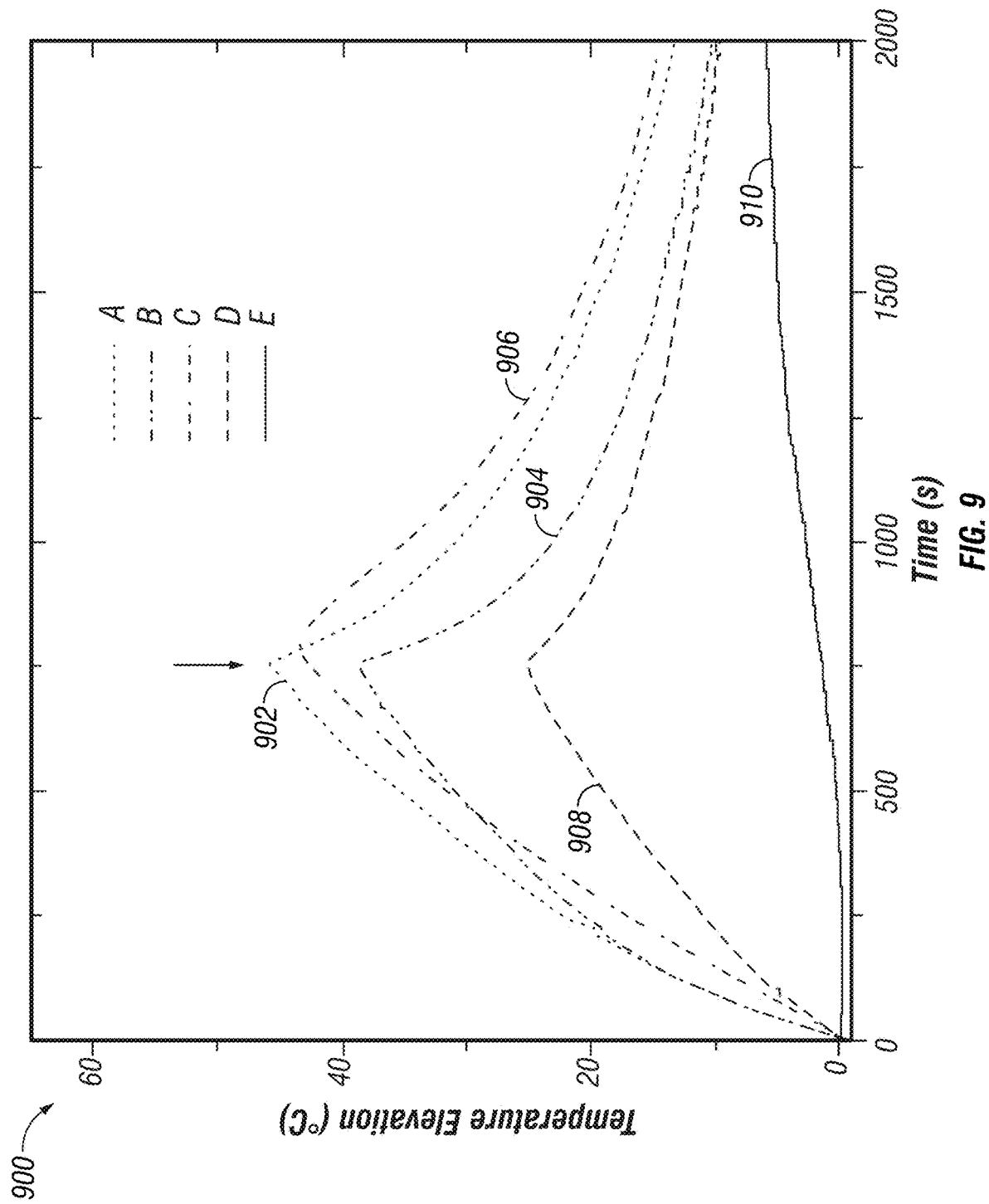
FIG. 9 depicts a graph illustrating temperature measurements of different areas of the prosthetic joint shown in FIG. 8.

FIG. 9 depicts a graph 900 illustrating one or more temperature measurements taken in the different areas of the prosthetic knee joint 800 shown in FIG. 8. In the embodiment shown, after approximately 750 seconds of heating exposure, a primary joint area temperature 902, a secondary joint area temperature 904, and a plastic spacer temperature 906 are within a few degrees of each other and have been elevated approximately 40° C. above a baseline temperature. However, in the embodiment shown, a close tissue area temperature 908 is only elevated approximately 20° C. above the baseline temperature and a far tissue area temperature 910 is only elevated <10° C. above the baseline temperature. Therefore, graph 900 illustrates that prosthetic knee joint 800 may be effectively heated via pulsed heating to a temperature suitable for biofilm treatment while realizing a temperature buffer between the temperature of prosthetic knee joint 800 and surrounding tissue areas 808 and 810. These results may illustrate that it may be feasible to achieve a desired treatment temperature on the surface of a metal implant in a relatively short time period, that thermal conduction may also create a desired treatment temperature on a plastic spacer surface that may be due to its direct contact with the metal implant components, and that a measurable temperature drop off may occur in the adjacent tissue, with the tissue having a safe temperature even within a few mm from the implant.

Figure 10:
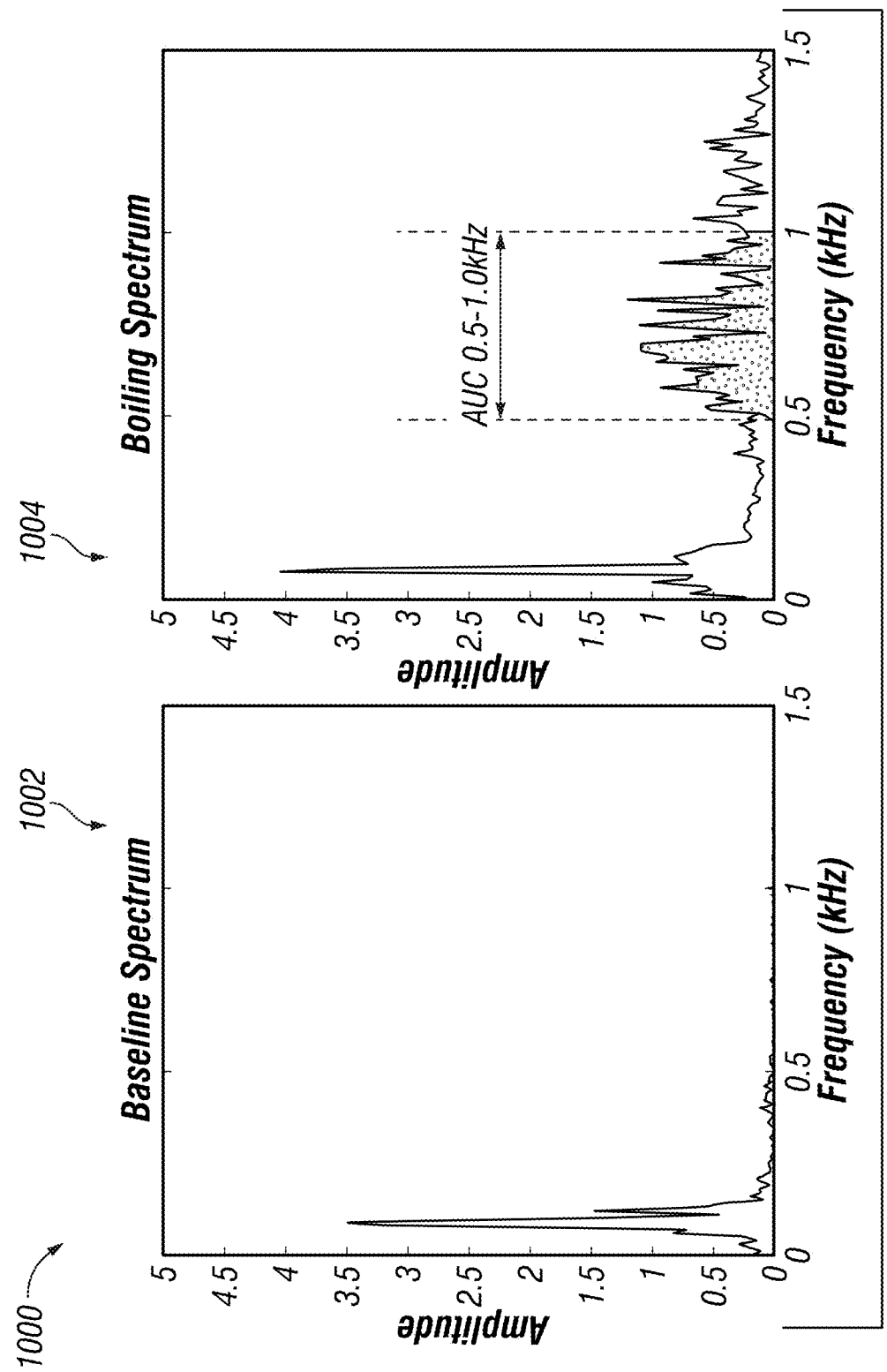
FIG. 10 depicts graphs illustrating acoustic emissions of non-boiling and boiling tissue temperatures according to an embodiment of the disclosure.

FIG. 10 depicts graphs 1000 illustrating one or more acoustic emissions of non-boiling and boiling tissue temperatures during AMF exposures according to an embodiment of the disclosure. In the embodiment shown, graphs 1000 show results from a test system including a solenoid, a fiber optic temperature system, and an acoustic hydrophone. A fiber optic temperature sensor was bonded to the surface of a metal ring placed inside a plastic tube containing water. The plastic tube was placed inside the solenoid and exposed to varying strengths and durations of alternating magnetic fields. The acoustic hydrophone was placed remotely to the plastic tube with a fluid contact to enable transmission of sound to the hydrophone. In the embodiment shown, graph 1002 shows a frequency spectrum of an acoustic signal measured using the hydrophone during an AMF exposure where the heating was not sufficient to generate tissue boiling. Graph 1004 shows a frequency spectrum of an acoustic signal during an AMF exposure where tissue temperatures approached a tissue boiling point. In the embodiment shown, a clear increase in acoustic energy is shown in graph 1004 for frequencies of approximately 500 Hz (0.5 kHz) and above. As an example, an AUC can be calculated between 500 and 1000 Hz. In some embodiments, this may enable a threshold to be assigned to signify the presence of tissue boiling.

Figure 11:
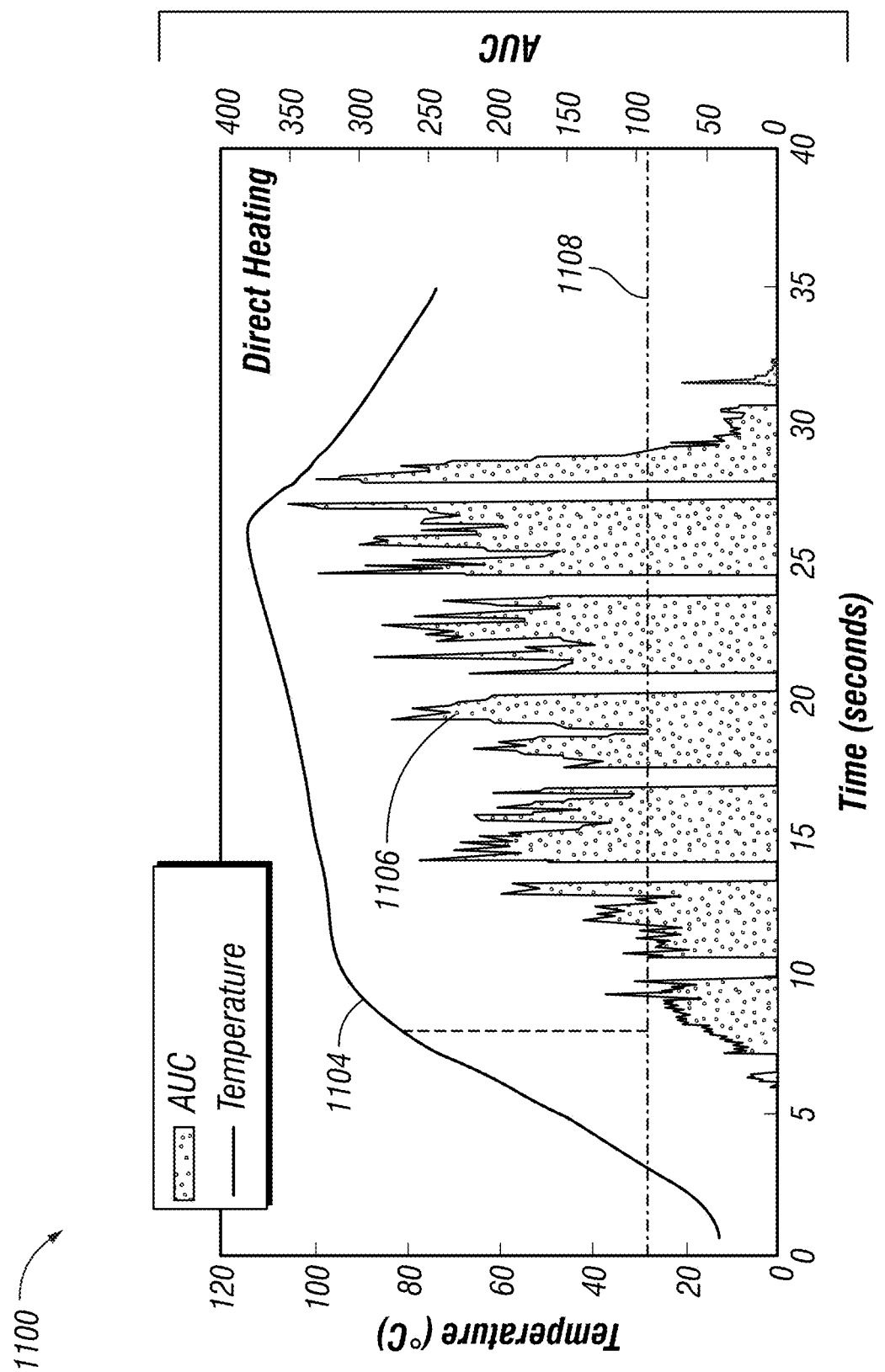
FIG. 11 depicts graphs illustrating acoustic emissions resulting from continuous heating and pulsed heating according to an embodiment of the disclosure.
Figure 11:
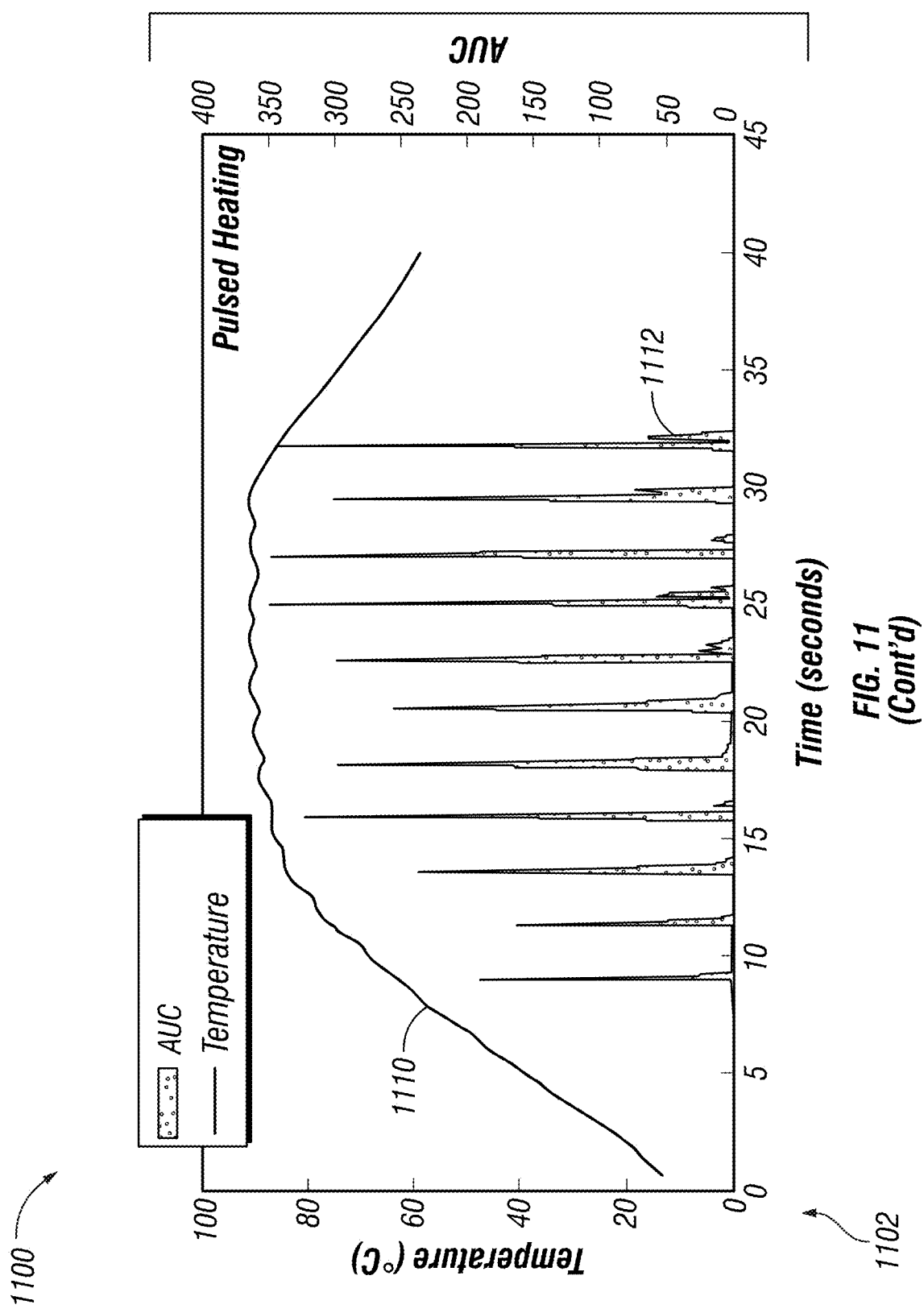

FIG. 11 depicts graphs 1100 and 1102 illustrating a relationship between acoustic emissions and temperature resulting from continuous heating and pulsed heating according to an embodiment of the disclosure. In the embodiment shown, graph 1100 shows an implant surface temperature 1104 and one or more acoustic signatures 1106 measured when a metal object is directly heated by exposure to continuous AMF. In the embodiment shown, once implant surface temperature 1104 exceeds 80° C., acoustic signatures 1106 pass a pre-defined threshold 1108, shown as an AUC of 100 (in this example, arbitrary units). In the embodiment shown, graph 1102 shows an implant surface temperature 1110 and one or more acoustic signatures 1112 measured when a metal object is directly heated by exposure to AMF pulses. In some embodiments, control computer 102 may be programmed to provide a power level and pulse duration that may maintain the implant surface temperature at a desired temperature, such as a temperature around 80° C. This approach may result in maintaining a relatively stable implant surface temperature 1110 for a desired time period of treatment.

Figure 12:
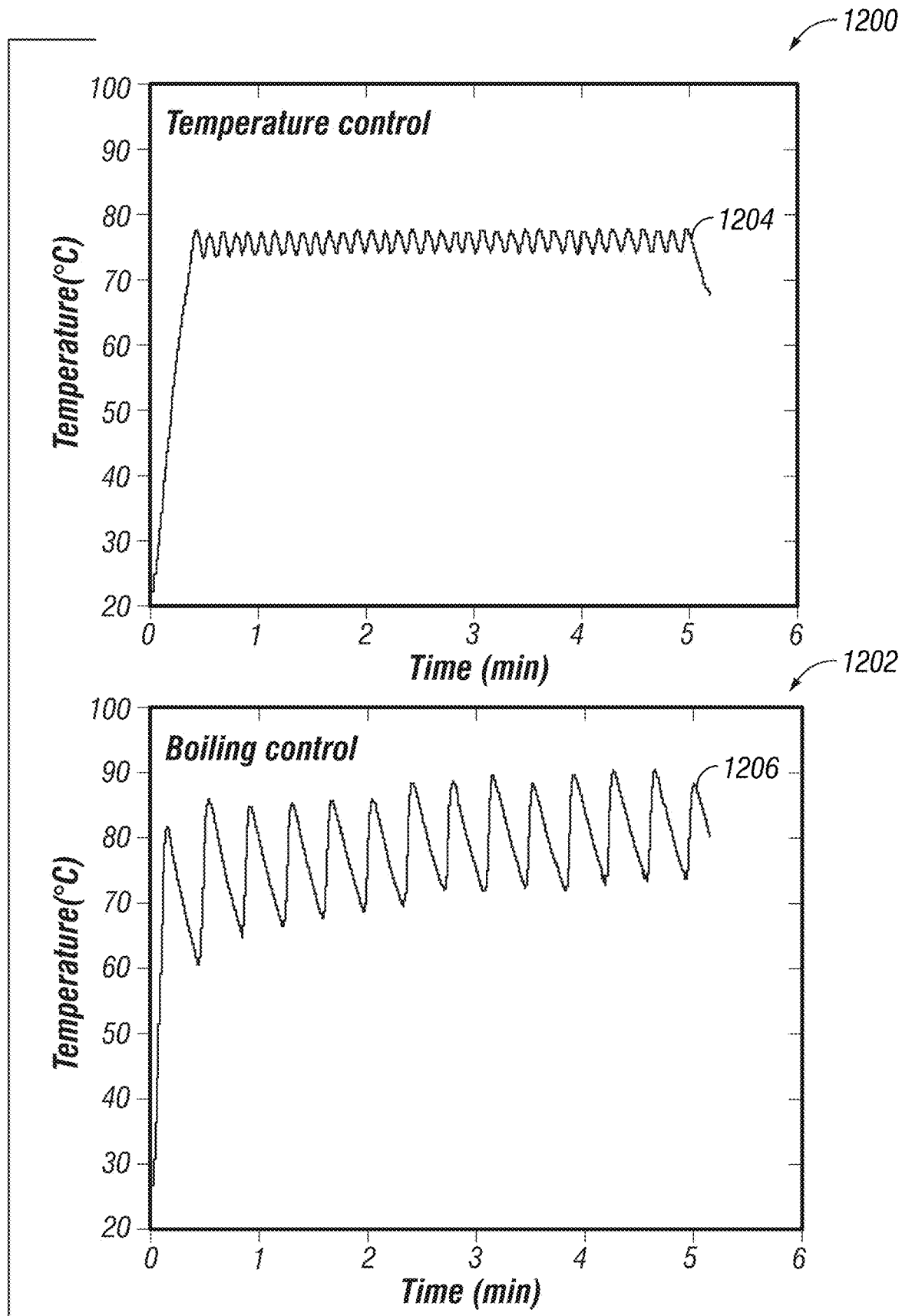
FIG. 12 depicts graphs illustrating temperature differences between temperature controlled heating methods and boiling control heating methods according to an embodiment of the disclosure.

FIG. 12 depicts graphs 1200 and 1202 illustrating temperature differences between temperature controlled heating methods and boiling control heating methods according to an embodiment of the disclosure. In the embodiment shown, graph 1200 shows results from an embodiment having one or more temperature sensors embedded into a metal implant that can be used to control AMF exposures and maintain an implant surface temperature 1204 near a desired target temperature. In the example shown, the target temperature was approximately 75° C. In the embodiment shown, graph 1202 shows results from an embodiment having one or more acoustic emission sensors that can be used to control AMF exposures based on the detection of one or more acoustic emissions related to tissue boiling at the implant surface. Upon detection of one or more acoustic emissions, a fixed delay period may be implemented (e.g., 20 s) before the AMF exposure is started again. This method may achieve a relatively uniform average temperature 1206 across the surface of the metal implant, albeit, with slightly greater temporal variations than shown in graph 1200. In the embodiment shown, a power of 100 W was used for the AMF exposures shown in both graphs 1200 and 1202 and the metal implant was a metal pin that was 5 mm in diameter and 10 mm in length.

Figure 13A:
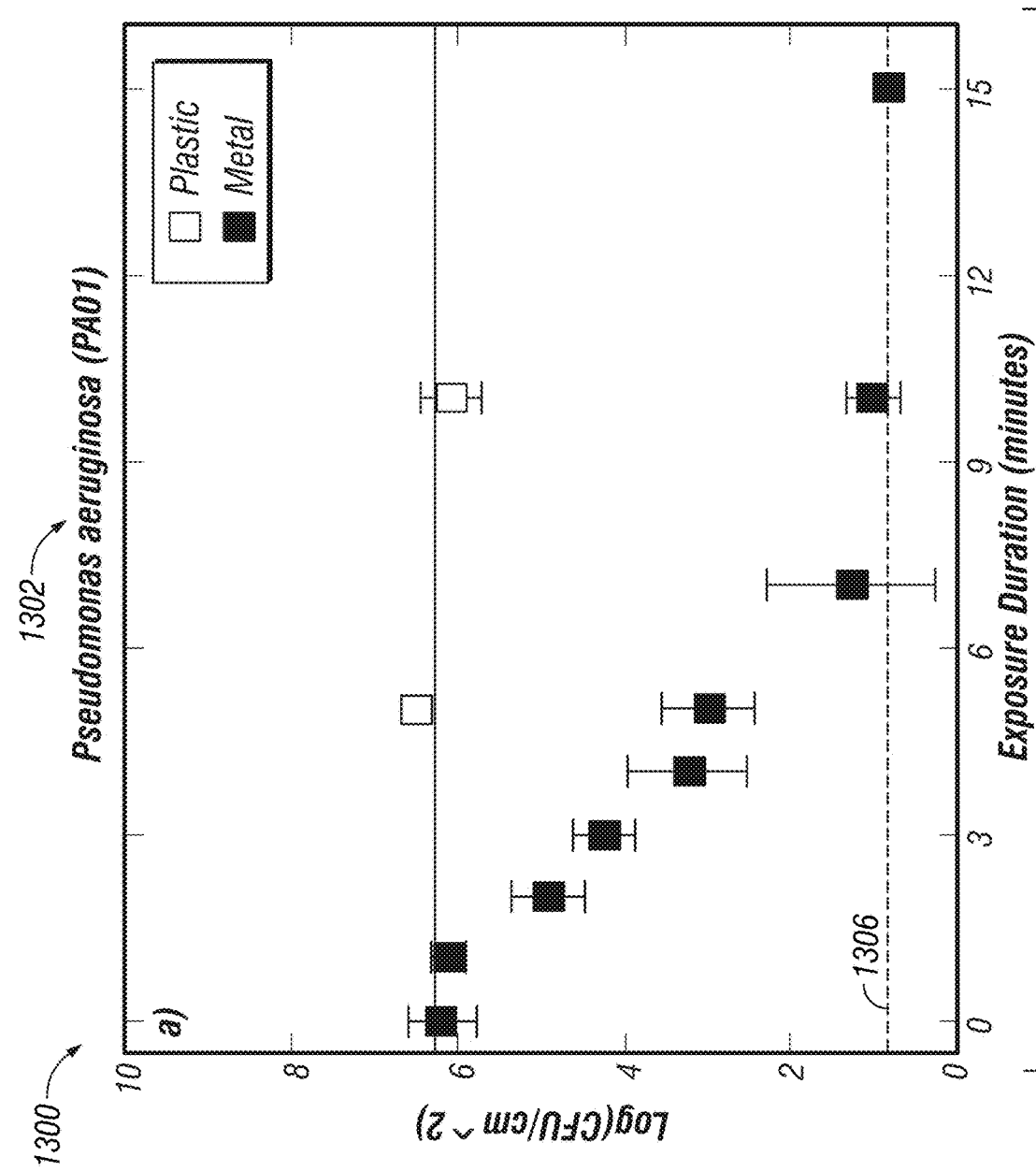
FIG. 13A depicts graphs illustrating effects of the duration of AMF continuous heating on exemplary biofilms according to an embodiment of the disclosure.
Figure 13A:
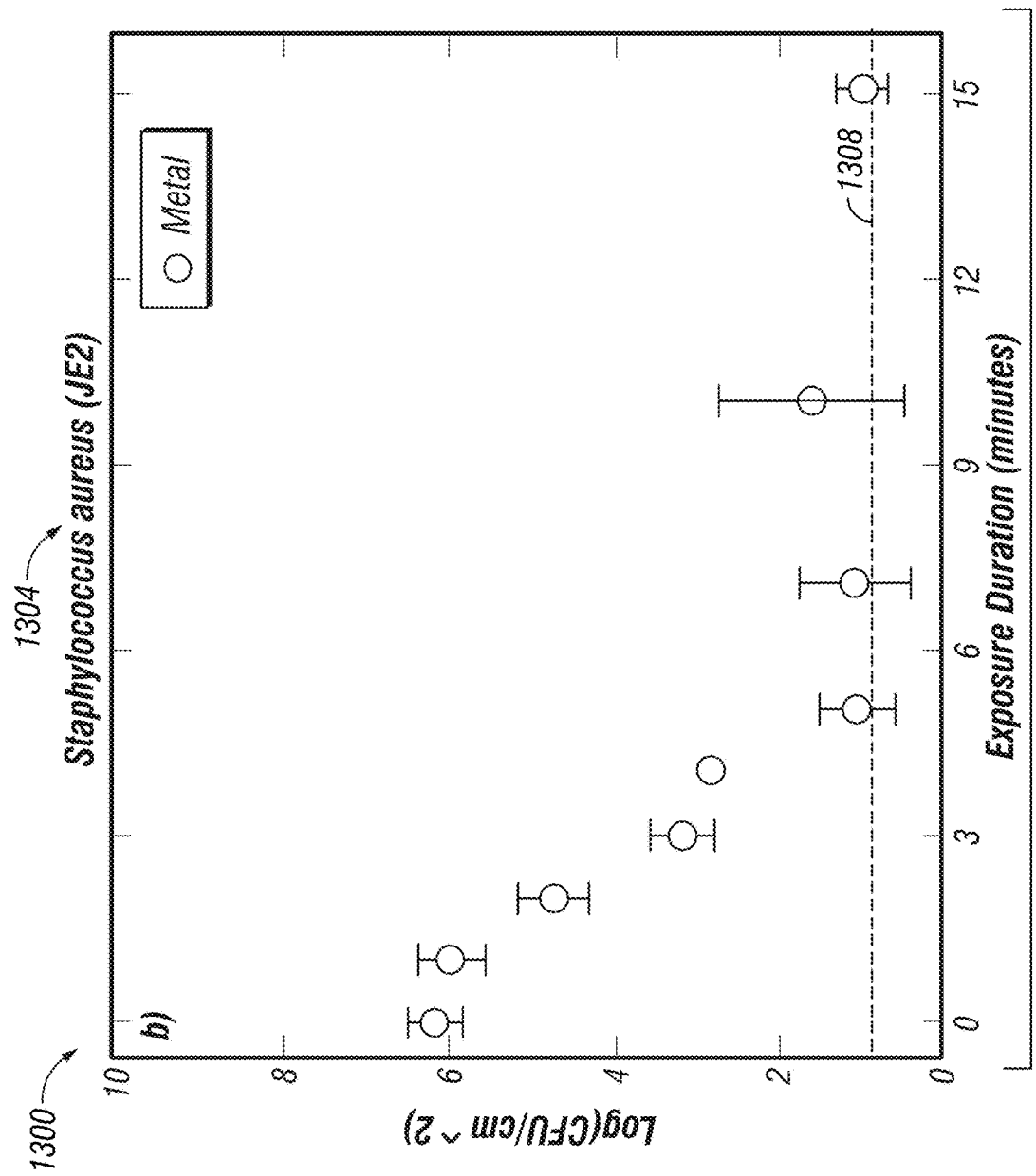

FIG. 13A depicts graphs 1300 illustrating effects of the duration of AMF continuous heating on exemplary biofilms according to an embodiment of the disclosure. In the embodiment shown, two different strains of bacterial biofilm were each grown on a separate metal washer. A control biofilm was also grown on a similarly sized plastic washer. Each of the washers was then exposed to a 20 W continuous AMF for varying durations and the number of bacteria associated with each biofilm was enumerated. In graphs 1302 and 1304, a bactericidal effect of the AMF as a function of exposure duration is shown for the two strains of biofilm grown on the washers. The graph 1302 shows a number of the bacteria *Pseudomonas aeruginosa* (PA01) remaining on a metal washer and a control plastic washer plotted as a function of the AMF exposure duration applied to the washers. Similarly, the graph 1304 shows a number of the bacteria *Staphylococcus aureus* (JE2) plotted as a function of the AMF exposure duration applied to a metal washer. For example, in graph 1302, the number of PA01 bacteria on the metal washer and the plastic washer was measured at various time intervals of AMF exposure. As shown in graph 1302, as the exposure duration increases past 1 minute, an increased steady reduction rate in bacterial number on the metal washer was exhibited. Also as shown in graph 1302, a significant reduction in total bacterial number was observed after 2 minutes of AMF exposure. Also as shown in graph 1302, at an exposure time between 5 and 7 minutes, an approximate 5 log reduction in the number of bacteria on the metal washer was exhibited. A similar effect is shown in graph 1304 for JE2 bacteria on a metal washer. The limit of detection (LOD) for the counting assay is shown in each graph as the dashed black lines 1306, 1308. However, as shown in graph 1302, the number of bacteria on the control plastic washer essentially remained constant at the initial value, with no significant increases or decreases throughout the exposure duration. This result serves to confirm that the bactericidal effect achieved on the metal washers is due to direct heating of the metal washers by the continuous AMF.

Figure 13B:
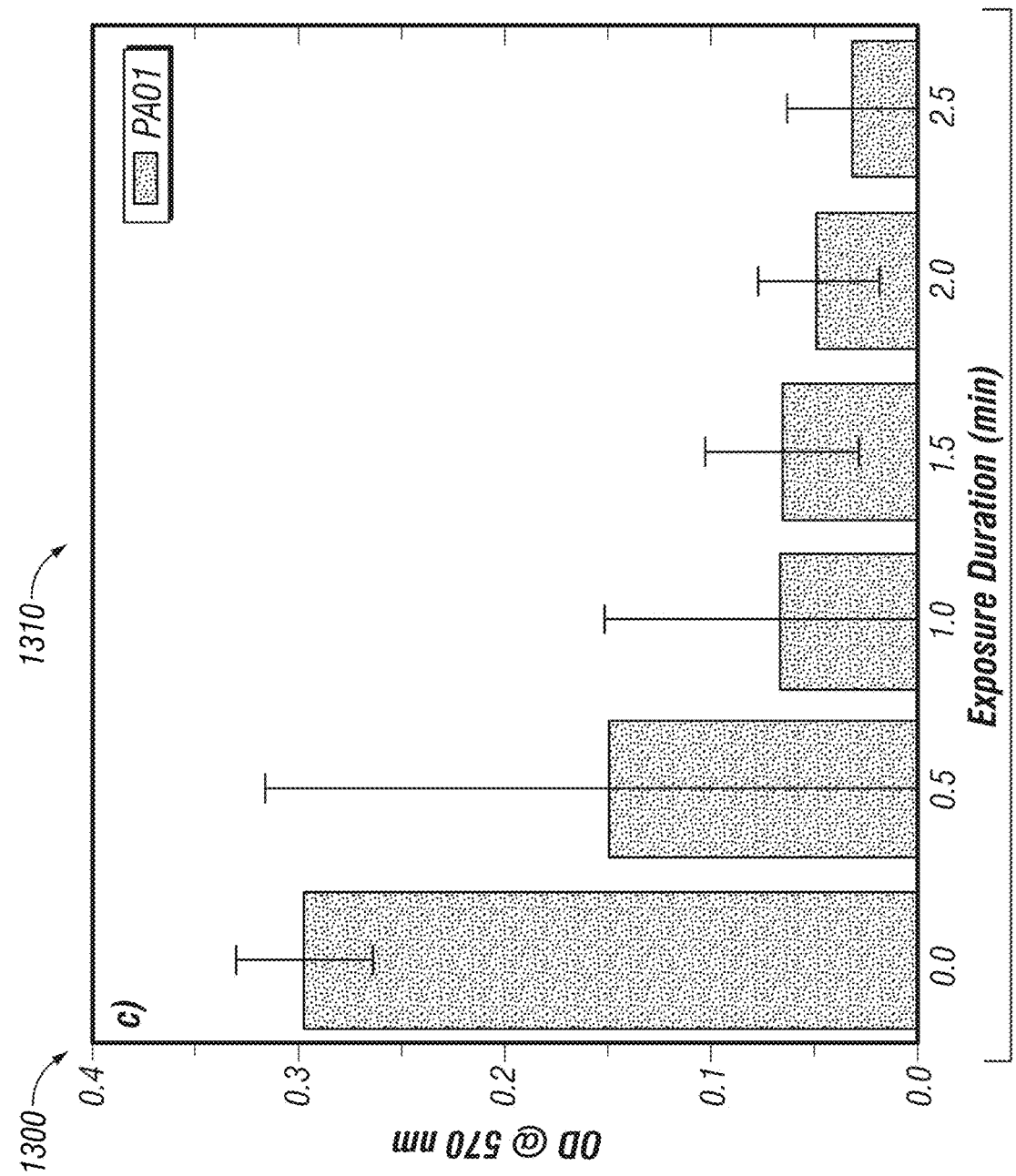
FIG. 13B depicts graphs illustrating effects of AMF continuous heating on matrix components of an exemplary biofilm as well as the influence of AMF exposures on the sensitivity of biofilm to exemplary antimicrobial agents according to an embodiment of the disclosure.
Figure 13B:
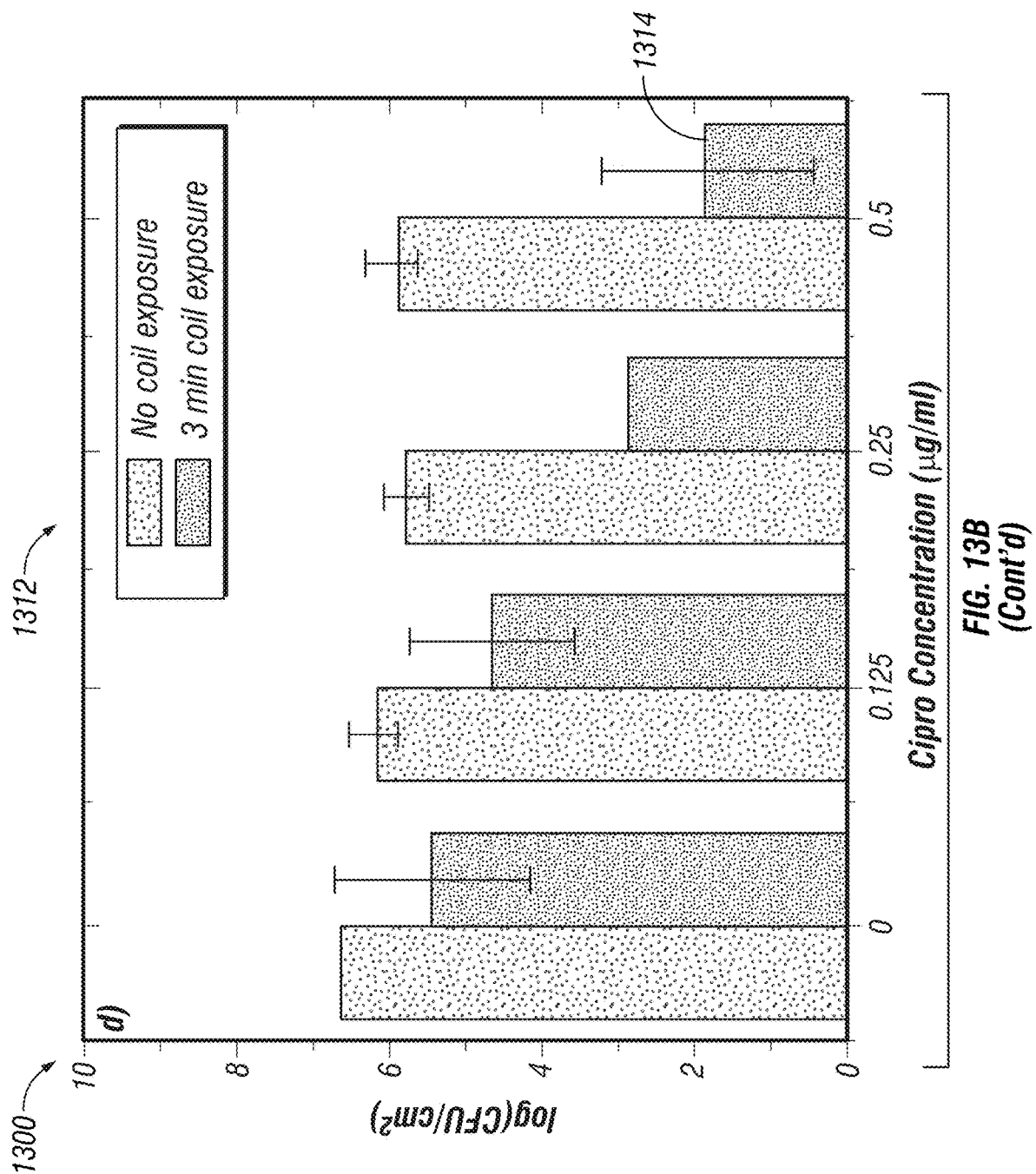

FIG. 13B depicts graphs 1300 illustrating effects of AMF exposures on the matrix components of a biofilm and the resulting sensitivity to exemplary antibiotic/antimicrobial agents. As discussed above, the AMF treatment processes according to the embodiments of the disclosure can be used in combination with antibiotic/antimicrobial regimens to increase the effectiveness of the antibiotic/antimicrobial agents and/or decrease the amount of time that the antibiotic/antimicrobial agents need to eradicate biofilms on the surface of a metallic implant. In the embodiment shown in graph 1310, the amount of biofilm matrix components were quantified for different AMF exposure times using a crystal violet staining technique. In this technique, the crystal violet stain can bind to the biofilm matrix and can be quantified as an optical density at 570 nm. In this technique, the amount of matrix components in the biofilm becomes greater as the optical density increases. As shown in graph 1310, a dose-dependent reduction in the PA01 biofilm matrix was achieved as the AMF exposure duration increased. Further, the reduction in the biofilm matrix commenced well before the reduction in bacteria number shown in FIG. 13A was realized. As shown in graph 1310, the bacterial number was reduced by about 50% after a 30 second AMF exposure. As shown in graph 1310, the bacterial number was reduced by about another 50% after a 1 minute AMF exposure. A decrease in the bacterial number continued with increasing AMF exposure duration until the LOD was reached after approximately 2.5 minutes of AMF exposure.

A similar effect is illustrated in the embodiment shown in graph 1312. As compared to graph 1302, graph 1312 shows that the number of bacteria can be reduced at a faster rate when a combination of AMF exposure and antibiotic/antimicrobial agents is used. As shown in graph 1302, the bacterial level approached the LOD 1306 at an AMF exposure time between 5 and 7 minutes and definitively reached the LOD 1306 by an AMF exposure time between 10 and 15 minutes without combined treatment with antibiotic/antimicrobial agents. In the embodiment shown in graph 1312, increasing concentrations of the antibiotic ciproflaxin were applied to metal washers having PA01 biofilm subjected to no AMF exposure and a 3 minute AMF exposure, respectively. The ability of the initial 3 minute AMF exposure to sensitize the PA01 biofilm to the antibiotic ciproflaxin is shown as a function of the concentration of ciproflaxin. As shown in graph 1312, a 5 log reduction in bacterial number was observed for the washer that received the prior 3 minute AMF pulse as the concentration of ciproflaxin reached 0.5 µg/ml at the LOD 1314. For the washer that didn't receive the prior AMF exposure, there was far less impact on the number of bacteria associated with the biofilm at the same concentration of ciproflaxin. As shown, the concentrations of ciprofloxacin used in this embodiment are not therapeutic for reducing this particular biofilm without previously exposing it to the initial AMF exposure. In this way, the medication's therapeutic effect on the biofilm can be increased at lower dosage amounts.

Figure 14A:
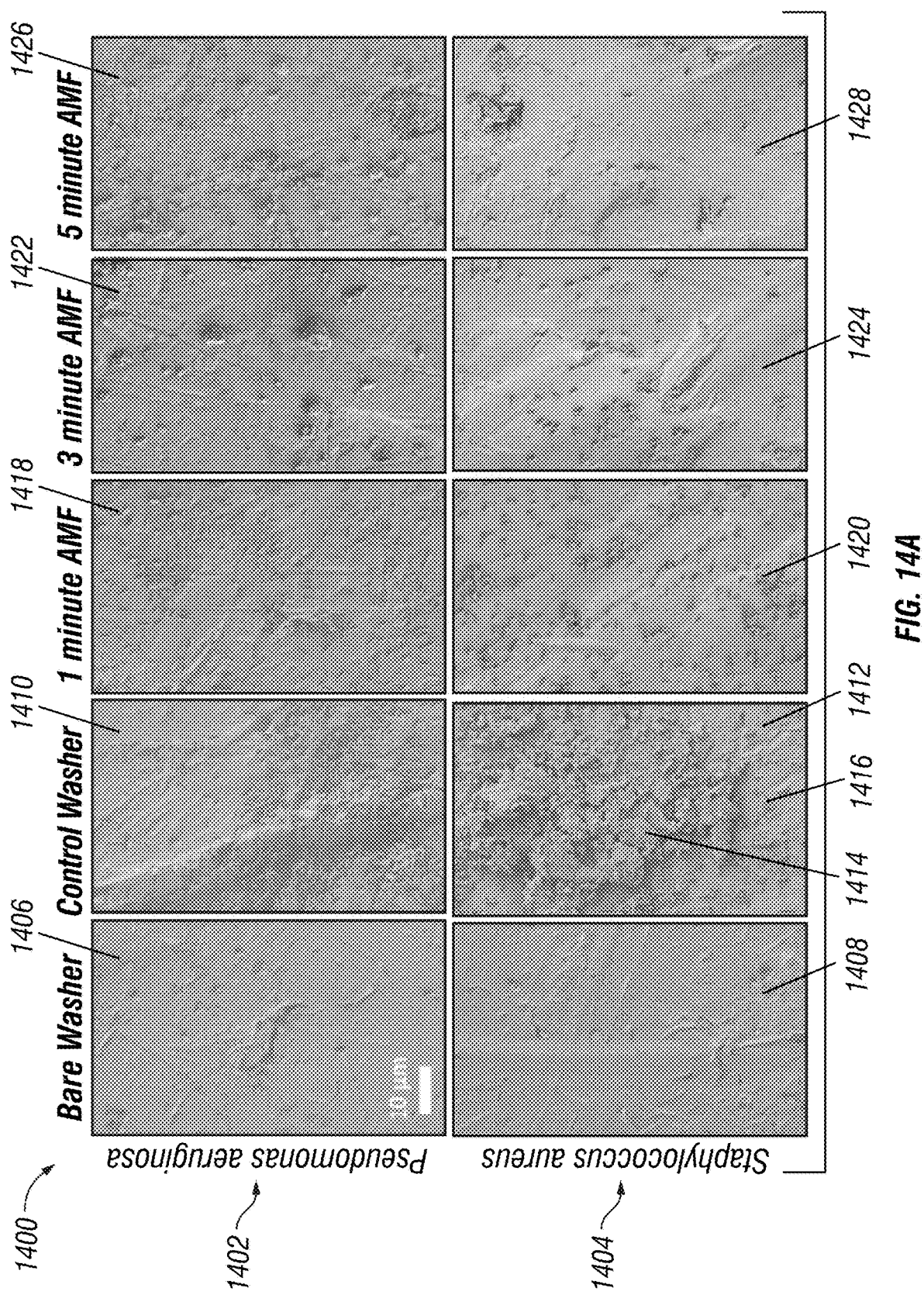
FIG. 14A depicts scanning electron microscope photos of exemplary biofilms under different control and AMF continuous heating conditions according to an embodiment of the disclosure. Exemplary time dependent effects of AMF continuous heating on the matrix components and bacteria within the biofilm are shown.

FIG. 14A depicts photos 1400 taken by a scanning electron microscope of exemplary biofilms under different control and AMF continuous heating conditions according to an embodiment of the disclosure. Specifically, photos 1400 show the effect of AMF exposure on both the extracellular polymeric substance (EPS) and the bacteria of the biofilm. The photos in row 1402 correspond to various metal washers coated with a PA01 biofilm and the photos in row 1404 correspond to various metal washers coated with a JE2 biofilm. The photos in rows 1402 and 1404 correspond to the graphs 1302 and 1304, respectively, shown in FIG. 13A. Each row contains images of the metal washers after exposure to different durations of continuous AMF. For comparison, a bare/negative washer not coated with biofilm is shown in photos 1406, 1408 and a positive control washer coated with biofilm but not exposed to AMF is shown in photos 1410, 1412. As seen in photo 1412, the biofilm is comprised of both EPS 1414 and bacteria 1416. Photos 1418, 1420 show the washers coated in biofilm after 1 minute of AMF exposure. As shown in photos 1418, 1420, the EPS has been significantly reduced even though a number of bacteria are still visible on the washer surface. Photos 1422, 1424 show the washers coated in biofilm after 3 minutes of AMF exposure. As shown in photos 1418, 1420, the EPS is barely visible and the number of bacteria has been significantly reduced from the number shown in photos 1418, 1420. For exposures greater than 3 minutes, it was difficult to find any viable bacteria on the washers and only scattered aggregates of EPS material were visible on the washer surface. Photos 1426, 1428 show the washers coated in biofilm after 5 minute of AMF exposure. As shown in photos 1426, 1428, the EPS and the number of bacteria have both been further reduced to achieve a comparative level to the bare washer shown in photos 1406, 1408.

Figure 14B:
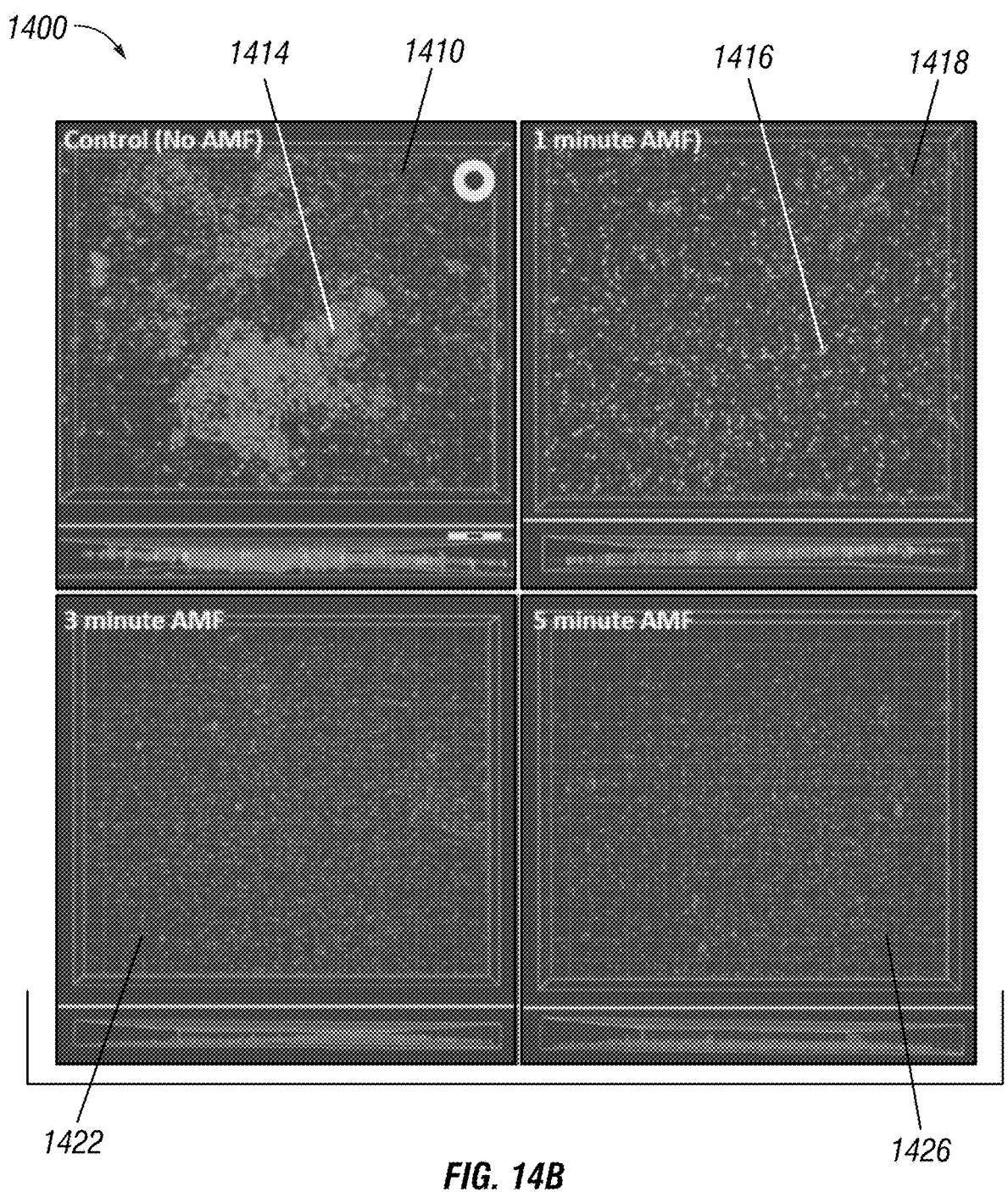
FIG. 14B depicts confocal microscope photos of exemplary biofilms under different control and AMF continuous heating conditions according to an embodiment of the disclosure. Exemplary time dependent effects of AMF continuous heating on the matrix components and bacteria within the biofilm are shown.

FIG. 14B depicts photos 1400 taken by a confocal microscope of exemplary biofilms under different control and AMF continuous heating conditions according to an embodiment of the disclosure. In the embodiment shown, photos 1400 correspond to the photos shown in row 1402 of FIG. 14A of metal washers coated with a PA01 biofilm formed by incubating the washers in GFP-PA01 for 18 hours. As shown in FIG. 14B, the washers exhibited a reduction in the amount of EPS biofilm matrix 1414 and the number of bacteria 1416 as the duration of AMF exposure was increased. In photo 1410, a large amount of the EPS and a large number of bacteria are both visible before any exposure to AMF. In photo 1418, while the number of bacteria shown remains similar to that shown in photo 1410, the amount of EPS has been significantly reduced after 1 minute of AMF exposure. In photo 1422, the EPS is barely visible and the number of bacteria has been significantly reduced from that shown in photo 1418 after 3 minutes of AMF exposure. In photo 1426, it was difficult to detect EFS and bacteria on the washer surface after 5 minutes of AMF exposure.

Although the embodiments shown in FIGS. 13A-14B were only exposed to continuous AMF, similar results may be achieved via exposure to a sequence of AMF pulses as previously described. Based on the results disclosed herein, some embodiments can be configured to apply one or more AMF pulses to a foreign metallic implant for one or more of a predetermined time period, pulse duration, pulse repetition frequency, and at a predetermined power level and receive one or more signals from one or more external acoustic sensor devices that correspond to one or more acoustic emission signatures emitted from the tissue surrounding the implant. When the control system detects acoustic emission signatures that indicate that the temperature of the foreign metallic implant is sufficient to disrupt a biofilm matrix on a surface of the foreign metallic implant, the control system can enable and/or present an indication that one or more antibiotic or antimicrobial treatments can be applied to the foreign metallic implant in order to achieve optimal effectiveness in reducing and/or eliminating the biofilm matrix and the number of bacteria or other microbes contained therein. In some embodiments, the system may be configured to reapply one or more AMF pulses to the foreign metallic implant when the one or more signals correspond to one or more acoustic emission signatures that indicate that a temperature of the foreign metallic implant is insufficient to disrupt the biofilm matrix on the surface of the foreign metallic implant. In some embodiments, the system may be configured to determine that the one or more signals correspond to one or more acoustic emission signatures that indicate that the temperature of the foreign metallic implant is sufficient to reduce and/or eliminate a number of bacteria on the surface of the foreign metallic implant.

Figure 15A:
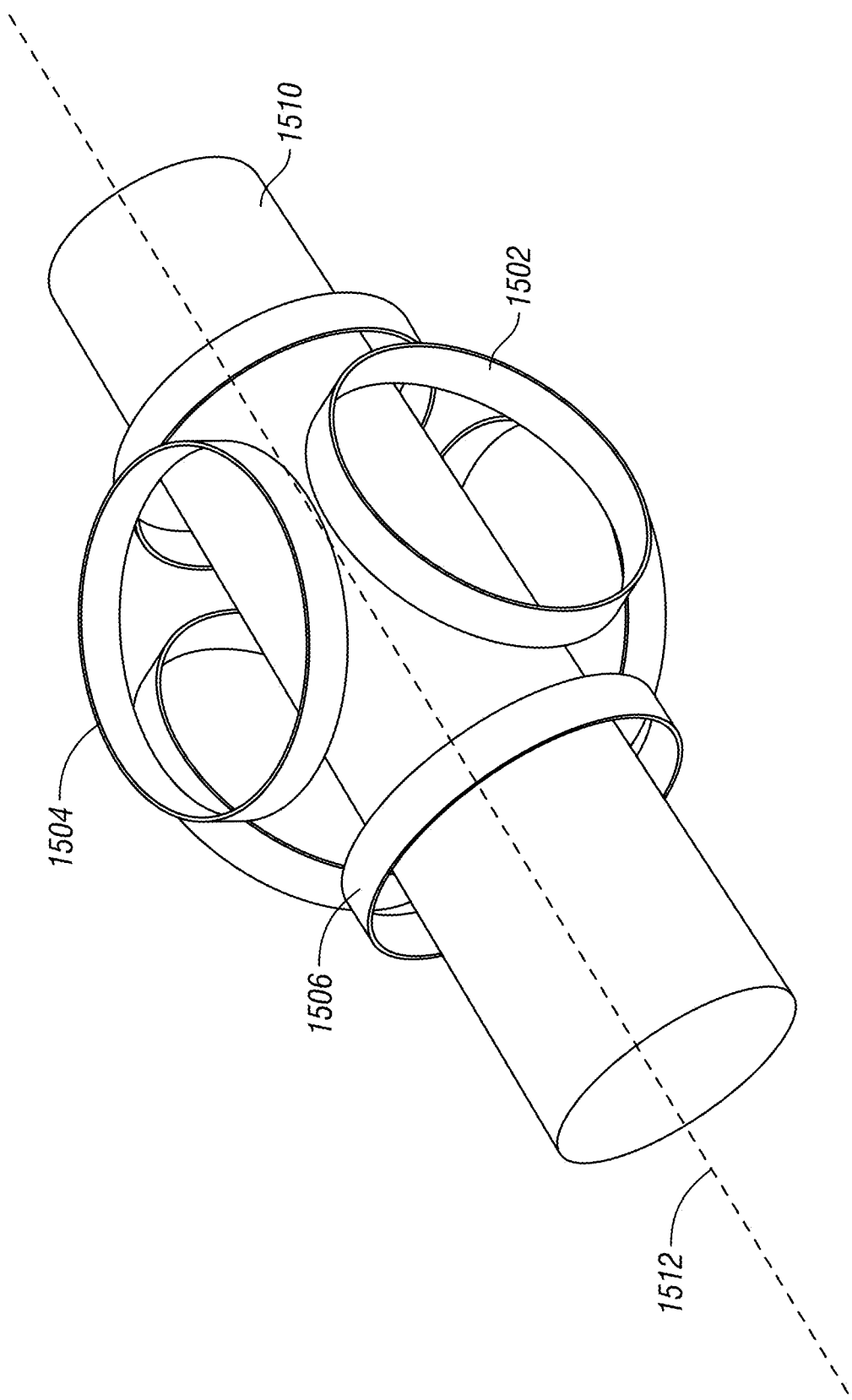
FIGS. 15A-15C depict various views of an exemplary AMF transmitter having a multiple coil arrangement according to an embodiment of the disclosure.
Figure 15B:
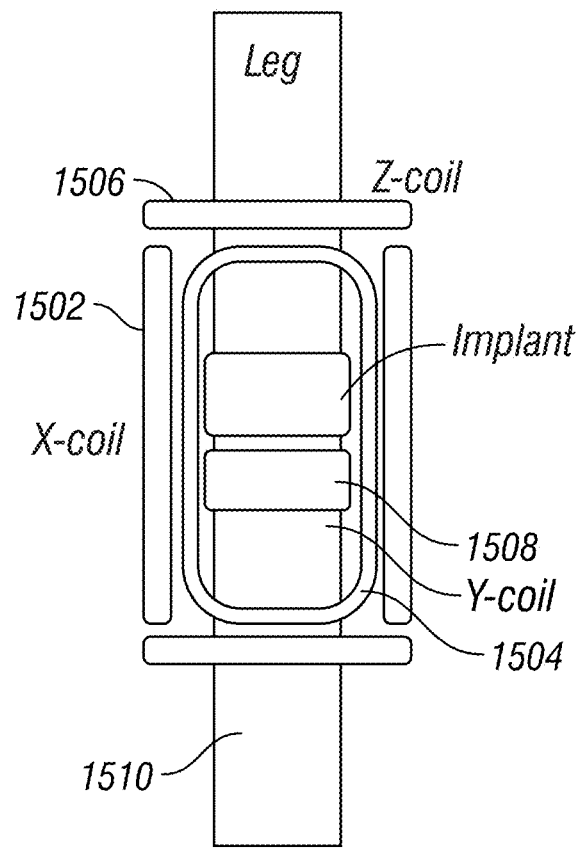
Figure 15C:
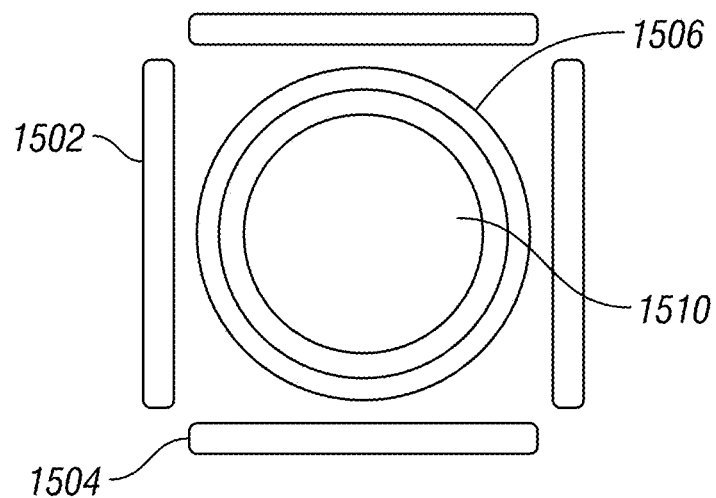

FIGS. 15A-15C depict various views of an exemplary multiple coil AMF transmitter 1500 according to an embodiment of the disclosure. In the embodiment shown in FIG. 2 discussed previously, the AMF transmitter may have a single coil that may be a solenoid coil 206. However, a solenoid coil 206 can only apply a uniform magnetic field along its inner axis. In the embodiments shown, a pattern of heating of the metallic implant depends on the direction of the applied magnetic field and the shape of the implant. Different parts of the metallic implant may be heated depending on the implant's position within the magnetic field. Therefore, it may be desirable to be able to rotate the magnetic field and apply the magnetic field to the implant in multiple directions and/or at different times. In the embodiment shown in FIGS. 15A-15C, the AMF transmitter 1500 can comprise a multiple coil arrangement that can apply a magnetic field to a foreign metallic implant in multiple directions and/or at different times.

With reference to a Cartesian coordinate system, in the embodiment shown in FIGS. 15A-15C, AMF transmitter 1500 includes at least one x-coil 1502 that applies a magnetic field in the x-direction, at least one y-coil 1504 that applies a magnetic field in the y-direction, and at least one z-coil 1506 that applies a magnetic field in the z-direction. In the embodiment shown, each of x-coils 1502, y-coils 1504, and z-coils 1506 form opposing pairs around a metallic implant 1508 contained in a body part such as a leg 1510. In the embodiment shown, each coil that forms an opposing pair is disposed in planes parallel to each other although other suitable planes can be used. Each pair of opposing x-coils 1502, y-coils 1504, and z-coils 1506 may produce a magnetic field between them in each respective Cartesian direction. In this way, a uniform magnetic field can be applied to implant 1508 in three orthogonal directions. By applying AMF pulses intermixed with waiting time periods as described previously, the AMF transmitter 1500 can achieve a more efficient heating distribution on the implant 1508 while avoiding overheating through the application of a magnetic field from three orthogonal directions than the single direction applied by solenoid coil 206. In some embodiments, AMF pulses can be applied simultaneously in all three orthogonal directions. In some embodiments, an AMF pulse can be applied in a first orthogonal direction. During a waiting period where an AMF pulse is not applied in the first orthogonal direction, an AMF pulse can be applied in one or more other orthogonal directions different than the first orthogonal direction.

In some embodiments, AMF transmitter 1500 can be rotated about a longitudinal axis 1512 of implant 1508 in order to apply a magnetic field from three orthogonal directions at different positions and/or different times around the longitudinal axis 1512. In the embodiment shown, as AMF transmitter 1500 rotates about longitudinal axis 1512, the positions of x-coils 1502 and/or y-coils 1504 can change relative to the implant 1508 while the positions of z-coils 1506 remain constant. In some embodiments, AMF transmitter 1500 may be rotatable around other and/or additional rotational axes to provide AMF pulses from additional directions. In some embodiments, AMF transmitter 1500 can remain in a fixed position to apply AMF pulses in one or more fixed directions while the position of implant 1508 and/or a patient can be changed or rotated between coils 1504, 1506, 1508. In some embodiments, one or more ferromagnetic materials may be provided. As AMF transmitter 1500 applies AMF pulses in one or more directions, the one or more ferromagnetic materials may be moved around implant 1508 and/or a patient to shape the magnetic field and modify the field distribution around implant 1508. One or more of these configurations may be used to modify the directions and/or the timing of the applied AMF pulses.

In the embodiment shown, each of x-coils 1502, y-coils 1504, and z-coils 1506 may be provided in a single housing. However, multiple other suitable arrangements may be used. In another embodiment, AMF transmitter 1500 may be implemented as a birdcage coil similar to those used in magnetic resonance imaging (Mill) applications. A birdcage coil embodiment may provide a circular or radial magnetic field to implant 1508. Some other suitable embodiments of AMF transmitter 1500 may provide both radial and Cartesian orthogonal magnetic fields.

Figure 16:
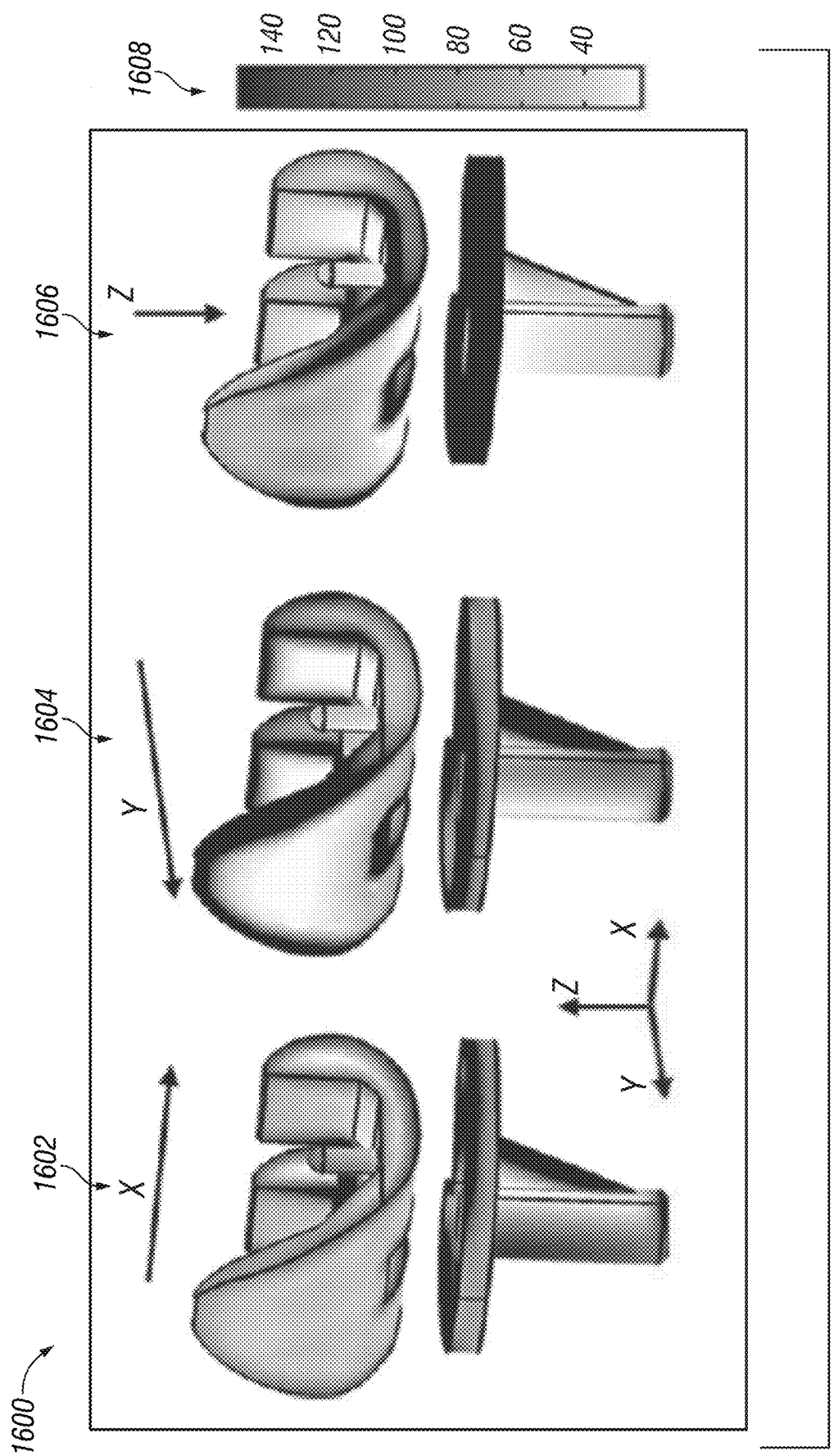
FIG. 16 depicts an exemplary metallic implant heating pattern when an exemplary alternating magnetic field is applied along different Cartesian directions according to an embodiment of the disclosure.

FIG. 16 depicts an exemplary metallic implant heating pattern 800 when a magnetic field is applied from different Cartesian directions according to an embodiment of the disclosure. In the embodiment shown, an exemplary 300 kHz AMF pulse was applied to a metallic implant surrounded by an air environment. In configuration 1602, the metallic implant was exposed to an alternating magnetic field in the x-direction. In configuration 1604, the metallic implant was exposed to an alternating magnetic field in the y-direction. In configuration 1606, the metallic implant was exposed to an alternating magnetic field in the z-direction. In the embodiment shown, heating scale 1608 represents a scale of temperature level in degrees Celsius and shows an increasing intensity of shading as the temperature increases. In the embodiment shown, each of the metallic implants was heated with a 1 second AMF pulse. As shown in configurations 1602, 1604, 1606, different portions of the metallic implant were heated to a high temperature based on the direction of the applied magnetic field. As such, configurations 1602, 1604, 1606 show that changing the applied magnetic field direction can change the spatial heating pattern on the implant. By combining these different magnetic field directions, such as with the embodiment shown in FIGS. 15A-15C, and by incorporating appropriate delays in between each AMF pulse, a more uniform overall heating of the implant can be achieved in a shorter time as compared to using only a magnetic field applied in a single principal direction.

It may be appreciated that the functions described above may be performed by multiple types of software applications, such as web applications or mobile device applications. If implemented in firmware and/or software, the functions described above may be stored as one or more instructions or code on a non-transitory computer-readable medium. Examples include non-transitory computer-readable media encoded with a data structure and non-transitory computer-readable media encoded with a computer program. Non-transitory computer-readable media includes physical computer storage media. A physical storage medium may be any available medium that can be accessed by a computer. By way of example, and not limitation, such non-transitory computer-readable media can comprise RAM, ROM, EEPROM, CD-ROM or other optical disk storage, magnetic disk storage or other magnetic storage devices, or any other physical medium that can be used to store desired program code in the form of instructions or data structures and that can be accessed by a computer. Disk and disc includes compact discs (CD), laser discs, optical discs, digital versatile discs (DVD), floppy disks and Blu-ray discs. Generally, disks reproduce data magnetically, and discs reproduce data optically. Combinations of the above are also included within the scope of non-transitory computer-readable media. Moreover, the functions described above may be achieved through dedicated devices rather than software, such as a hardware circuit comprising custom VLSI circuits or gate arrays, off-the-shelf semiconductors such as logic chips, transistors, or other discrete components, all of which are non-transitory. Additional examples include programmable hardware devices such as field programmable gate arrays, programmable array logic, programmable logic devices or the like, all of which are non-transitory. Still further examples include application specific integrated circuits (ASIC) or very large scale integrated (VLSI) circuits. In fact, persons of ordinary skill in the art may utilize any number of suitable structures capable of executing logical operations according to the described embodiments.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the disclosed methods, devices, and systems are not intended to be limited to the particular forms disclosed. Rather, they include all modifications and alternatives falling within the scope of the claims, and embodiments other than those shown may include some or all of the features of the depicted embodiment. For example, components may be combined as a unitary structure and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A system to treat a surface of a foreign metallic implant, the system comprising:
   one or more external transmitter devices comprising an alternating magnetic field (AMF) transmitter configured to apply one or more AMF pulses to the foreign metallic implant;
   one or more acoustic sensors configured to detect one or more acoustic waves having a frequency between 0 Hz and 1000 Hz; and
   a control system comprising at least one processor, the control system configured to:
      enable the one or more external transmitter devices to apply one or more AMF pulses to the foreign metallic implant with one or more of: (a) a predetermined time period, (b) a predetermined pulse duration, (c) a predetermined pulse repetition frequency, or (d) a predetermined power level; and
      receive one or more signals from the one or more sensors.

2. The system of claim 1, the control system being further configured to determine that the one or more signals indicate that a temperature of the foreign metallic implant is sufficient to disrupt a biofilm matrix on the surface of the foreign metallic implant.

3. The system of claim 1, the one or more acoustic sensors being configured to detect the one or more acoustic waves emitted from soft tissue adjacent to the foreign metallic implant when the soft tissue is heated to a particular temperature threshold.

4. The system of claim 1, the one or more acoustic sensors being configured to detect the one or more acoustic waves having a frequency between 500 Hz and 1000 Hz.

5. The system of claim 1 comprising one or more internal temperature sensors embedded into the surface of the foreign metallic implant.

6. The system of claim 1 comprising one or more external optical receiver devices configured to detect photons emitted from one or more thermoluminescent materials embedded into the surface of the foreign metallic implant, the one or more thermoluminescent materials configured to emit the photons upon sensing a temperature greater than a predetermined threshold on the surface of the foreign metallic implant.

7. A foreign metallic implant treatment apparatus comprising:
   a housing; and
   a plurality of AMF transmitters configured to apply one or more AMF pulses to the foreign metallic implant in three orthogonal directions,
   where the plurality of AMF transmitters are configured as pairs situated on opposing sides of the metallic implant in each of a Cartesian x-direction, y-direction, and z-direction.

8. The apparatus of claim 7, where each of the AMF transmitters in a pair are situated in parallel planes from each other.

9. The apparatus of claim 7, where at least one of the plurality of AMF transmitter pairs is configured to rotate around the foreign metallic implant and apply the one or more AMF pulses at different positions around the foreign metallic implant.

10. The apparatus of claim 7, further comprising one or more ferromagnetic materials configured to be movable around the foreign metallic implant.

11. A method of treating a foreign metallic implant, the method comprising:
   enabling, by a control system comprising at least one processor, one or more external transmitter devices comprising an AMF transmitter to apply one or more AMF pulses to the foreign metallic implant with one or more of a predetermined time period, a predetermined pulse duration, a predetermined pulse repetition frequency, or a predetermined power level;

receiving, by the control system, one or more signals from one or more acoustic sensors;

determining, by the control system, that the one or more signals indicate heating of the foreign metallic implant; and enabling, by the control system, an adjusting of at least one of a duration, a frequency, or an amplitude of the one or more AMF pulses based on the one or more signals.

12. The method of claim 11, comprising receiving, by the control system, one or more signals from one or more internal temperature sensors embedded into a surface of the foreign metallic implant.

13. The method of claim 11, comprising receiving, by the control system, one or more signals from one or more optical sensors comprising one or more external optical receiver devices to detect photons emitted from one or more thermoluminescent materials embedded into a surface of the foreign metallic implant, the one or more thermoluminescent materials configured to emit the photons upon sensing a temperature greater than a predetermined threshold on the surface of the foreign metallic implant.

14. The method of claim 11, further comprising:

enabling, by the control system, the one or more external transmitter devices to shut off upon receipt of the one or more signals.

15. The system of claim 1, wherein the AMF transmitter comprises at least one coil.

16. The system of claim 1, wherein the AMF transmitter comprises a phased array.

17. The system of claim 15, where at least one coil comprises one or more of a solenoid coil, a saddle coil, a pancake coil, or combinations thereof.

* * * * *